(12) United States Patent
Mullaney

(10) Patent No.: US 10,702,308 B2
(45) Date of Patent: *Jul. 7, 2020

(54) EXTERNAL FIXATION CLAMP USING A TRIGGER MECHANISM AND STORED SPRING ENERGY

(71) Applicant: Zimmer, Inc., Warsaw, IN (US)

(72) Inventor: Michael W. Mullaney, Naples, FL (US)

(73) Assignee: Zimmer, Inc., Warsaw, IN (US)

(*) Notice: Subject to any disclaimer, the term of this patent is extended or adjusted under 35 U.S.C. 154(b) by 164 days.

This patent is subject to a terminal disclaimer.

(21) Appl. No.: 15/843,749

(22) Filed: Dec. 15, 2017

(65) Prior Publication Data

US 2018/0103986 A1    Apr. 19, 2018

Related U.S. Application Data

(63) Continuation of application No. 15/053,580, filed on Feb. 25, 2016, now Pat. No. 9,888,943, which is a (Continued)

(51) Int. Cl.
*A61B 17/64* (2006.01)
(52) U.S. Cl.
CPC ................. *A61B 17/6466* (2013.01)
(58) Field of Classification Search
CPC ............................... A61B 17/64–6483
See application file for complete search history.

(56) References Cited

U.S. PATENT DOCUMENTS 1,706,215 A    3/1929 Davidson
2,705,603 A    4/1955 Bitz et al.
(Continued)

FOREIGN PATENT DOCUMENTS

CN    102018556 A    4/2011
CN    103687558 A    3/2014
(Continued)

OTHER PUBLICATIONS

"U.S. Appl. No. 13/471,998, Advisory Action dated May 1, 2014", 3 pgs.
(Continued)

*Primary Examiner* — Jacqueline T Johanas
*Assistant Examiner* — Michelle C Eckman
(74) *Attorney, Agent, or Firm* — Schwegman Lundberg & Woessner, P.A.

(57) ABSTRACT

An external fixation clamp for receiving a fixation element includes an inner jaw and an outer jaw movable between an open position that permits the fixation element to be placed between the inner and outer jaws and a closed position that restricts removal of the fixation element from between the inner and outer jaws. A latch assembly may cooperate with the inner and outer jaws to secure the jaws in a closed position. The latch assembly may comprise a latch and a latch biasing member. The latch may be configured to translate linearly relative to one of the inner and outer jaws, and the latch biasing member may have a first higher level of stored energy when the inner and outer jaws are in the open position and a second lower level of stored energy when the inner and outer jaws are in the closed position.

18 Claims, 17 Drawing Sheets

Related U.S. Application Data continuation of application No. 13/471,998, filed on May 15, 2012, now Pat. No. 9,277,937.

(60) Provisional application No. 61/487,154, filed on May 17, 2011.

(56) References Cited

U.S. PATENT DOCUMENTS

| | | | |
|---|---|---|---|
| 3,044,512 A | 7/1962 | Jones | |
| 3,154,331 A | 10/1964 | Engelhardt | |
| 3,373,465 A | 3/1968 | Johnson et al. | |
| 3,406,987 A | 10/1968 | Hunder et al. | |
| 3,580,512 A * | 5/1971 | Smith | F23D 14/64 239/432 |
| 4,037,978 A | 7/1977 | Connelly | |
| 4,115,966 A | 9/1978 | Delee et al. | |
| 4,312,488 A | 1/1982 | Pierron | |
| 4,388,747 A | 6/1983 | Plummer | |
| 4,483,334 A | 11/1984 | Murray | |
| 4,620,533 A | 11/1986 | Mears | |
| 4,653,481 A | 3/1987 | Howland et al. | |
| 4,662,365 A | 5/1987 | Gotzen et al. | |
| 4,700,437 A | 10/1987 | Hoshino | |
| 4,718,151 A * | 1/1988 | LeVahn | A61B 17/02 24/535 |
| D295,725 S | 5/1988 | Shioda | |
| 4,817,897 A | 4/1989 | Kreusel | |
| 5,020,195 A * | 6/1991 | LeVahn | A61B 17/02 24/514 |
| 5,242,240 A * | 9/1993 | Gorham | A61B 17/02 403/389 |
| 5,269,586 A * | 12/1993 | Hahn | B60J 7/1851 292/240 |
| 5,312,405 A | 5/1994 | Korotko et al. | |
| 5,427,465 A | 6/1995 | Sato | |
| 5,662,648 A | 9/1997 | Faccioli et al. | |
| 5,683,389 A | 11/1997 | Orsak et al. | |
| 5,709,681 A | 1/1998 | Pennig | |
| 5,727,899 A * | 3/1998 | Dobrovolny | A61B 17/02 403/384 |
| 5,741,252 A | 4/1998 | Mazzio et al. | |
| 5,746,741 A | 5/1998 | Kraus et al. | |
| 5,752,954 A * | 5/1998 | Mata | A61B 17/645 606/59 |
| 5,800,548 A | 9/1998 | Martin et al. | |
| 5,827,282 A | 10/1998 | Pennig et al. | |
| 5,860,728 A | 1/1999 | Maglica | |
| 5,891,144 A * | 4/1999 | Mata | A61B 17/6466 606/54 |
| 5,897,087 A * | 4/1999 | Farley | A61B 17/02 248/229.21 |
| 5,976,141 A | 11/1999 | Haag et al. | |
| 6,022,348 A | 2/2000 | Spitzer | |
| 6,033,363 A * | 3/2000 | Farley | A61B 17/02 600/234 |
| 6,042,174 A * | 3/2000 | Durrani | B60J 7/1851 292/DIG. 5 |
| 6,080,153 A | 6/2000 | Mata et al. | |
| 6,083,150 A * | 7/2000 | Aznoian | A61B 10/06 600/564 |
| 6,102,911 A | 8/2000 | Faccioli et al. | |
| 6,123,482 A * | 9/2000 | Keller | F16B 7/0493 403/290 |
| 6,168,345 B1 * | 1/2001 | Legge | E04G 7/14 182/179.1 |
| 6,217,577 B1 | 4/2001 | Hofmann | |
| 6,264,396 B1 | 7/2001 | Dobrovolny et al. | |
| 6,277,069 B1 * | 8/2001 | Gray | A61B 17/02 403/391 |
| 6,340,361 B1 * | 1/2002 | Kraus | A61B 17/171 606/54 |
| 6,342,054 B1 * | 1/2002 | Mata | A61B 17/62 606/54 |
| D455,831 S * | 4/2002 | Koros | F16M 13/022 D24/128 |
| 6,376,775 B1 | 4/2002 | Leijon et al. | |
| 6,386,786 B1 | 5/2002 | Perlman et al. | |
| 6,409,729 B1 | 6/2002 | Martinelli et al. | |
| 6,500,177 B1 | 12/2002 | Martinelli et al. | |
| 6,520,560 B2 * | 2/2003 | Schutt | B60J 7/1851 292/DIG. 5 |
| 6,547,789 B1 * | 4/2003 | Ventre | A61B 17/7032 606/305 |
| 6,613,049 B2 * | 9/2003 | Winquist | A61B 17/6466 606/54 |
| 6,637,082 B1 | 10/2003 | Chang | |
| 6,652,523 B1 | 11/2003 | Evrard et al. | |
| 6,702,814 B2 * | 3/2004 | Walulik | A61B 17/645 606/56 |
| 6,716,212 B1 * | 4/2004 | Pickens | A61B 17/645 606/54 |
| 6,736,775 B2 | 5/2004 | Phillips | |
| 6,834,907 B2 * | 12/2004 | Dietl | B60J 7/1851 292/DIG. 5 |
| 6,887,194 B2 | 5/2005 | Hart et al. | |
| 6,916,319 B2 * | 7/2005 | Munting | A61B 17/7043 606/250 |
| 7,004,943 B2 | 2/2006 | Ferrante et al. | |
| 7,048,735 B2 | 5/2006 | Ferrante et al. | |
| D526,410 S * | 8/2006 | Phillips | D24/135 |
| 7,114,888 B2 * | 10/2006 | Stankus | E21D 15/325 405/288 |
| 7,241,071 B2 | 7/2007 | Carraher et al. | |
| 7,241,074 B2 | 7/2007 | Thomke et al. | |
| 7,252,311 B2 * | 8/2007 | Pratt | B64D 29/06 292/113 |
| 7,261,713 B2 | 8/2007 | Langmaid et al. | |
| D551,763 S * | 9/2007 | Phillips | D24/135 |
| 7,314,331 B1 | 1/2008 | Koros et al. | |
| 7,320,556 B2 | 1/2008 | Vagn-erik | |
| 7,473,223 B2 | 1/2009 | Fetzer | |
| 7,491,008 B2 * | 2/2009 | Thomke | A61B 17/645 403/316 |
| 7,527,626 B2 | 5/2009 | Lutz et al. | |
| 7,553,279 B1 * | 6/2009 | Phillips | F16B 2/185 248/229.2 |
| 7,562,855 B2 * | 7/2009 | Oetlinger | F16B 7/0493 248/227.4 |
| 7,588,537 B2 | 9/2009 | Bass | |
| 7,708,736 B2 | 5/2010 | Mullaney | |
| 7,744,632 B2 | 6/2010 | Usher | |
| D633,207 S * | 2/2011 | Murner | D24/128 |
| D633,208 S * | 2/2011 | Murner | D24/128 |
| 7,887,537 B2 | 2/2011 | Ferrante et al. | |
| 7,931,650 B2 | 4/2011 | Winquist et al. | |
| 7,938,829 B2 | 5/2011 | Mullaney | |
| D663,030 S * | 7/2012 | Murner | D24/143 |
| 8,236,028 B2 | 8/2012 | Kalfas | A61B 17/705 606/246 |
| 8,343,166 B2 * | 1/2013 | Maughan | A61B 17/6466 606/105 |
| 8,430,916 B1 * | 4/2013 | Winslow | A61B 17/7001 606/250 |
| D682,426 S * | 5/2013 | Dominik | D24/143 |
| D683,461 S * | 5/2013 | Murner | D24/171 |
| 9,277,937 B2 | 3/2016 | Mullaney | |
| 9,888,943 B2 | 2/2018 | Mullaney | |
| 2001/0004432 A1 | 6/2001 | Pfister | |
| 2002/0026190 A1 * | 2/2002 | Walulik | A61B 17/645 606/57 |
| 2002/0037193 A1 * | 3/2002 | Gibbons | F16B 7/0433 403/344 |
| 2002/0042613 A1 | 4/2002 | Mata et al. | |
| 2002/0061225 A1 | 5/2002 | Boucher et al. | |
| 2002/0165543 A1 | 11/2002 | Winquist et al. | |
| 2002/0177754 A1 * | 11/2002 | Phillips | A61B 17/02 600/234 |
| 2003/0149429 A1 * | 8/2003 | Ferrante | A61B 17/645 606/59 |

(56) References Cited

U.S. PATENT DOCUMENTS

| | | | |
|---|---|---|---|
| 2003/0149430 A1* | 8/2003 | Ferrante | A61B 17/645 606/59 |
| 2003/0191467 A1* | 10/2003 | Hoffmann-Clair | A61B 17/6466 606/59 |
| 2003/0199738 A1* | 10/2003 | Yager | A61B 17/02 600/227 |
| 2003/0229273 A1* | 12/2003 | Mulac | A61B 17/02 600/234 |
| 2004/0092369 A1* | 5/2004 | Slawinski | A63B 21/00181 482/104 |
| 2004/0092931 A1* | 5/2004 | Taylor | A61B 17/7052 606/253 |
| 2005/0080321 A1* | 4/2005 | Bjork | A61B 1/32 600/230 |
| 2005/0085810 A1* | 4/2005 | Lutz | A61B 17/60 606/54 |
| 2005/0113831 A1 | 5/2005 | Franck et al. | |
| 2005/0245939 A1* | 11/2005 | Ferrante | A61B 17/6466 606/96 |
| 2006/0004360 A1* | 1/2006 | Kramer | A61B 17/7041 606/301 |
| 2006/0017566 A1 | 1/2006 | Gauvreau et al. | |
| 2006/0039750 A1* | 2/2006 | Thomke | A61B 17/645 403/385 |
| 2006/0058789 A1* | 3/2006 | Kim | A61B 17/7049 606/914 |
| 2006/0079899 A1* | 4/2006 | Ritland | A61B 17/7007 606/246 |
| 2006/0229602 A1 | 10/2006 | Olsen et al. | |
| 2006/0229603 A1 | 10/2006 | Olsen | |
| 2006/0229616 A1* | 10/2006 | Albert | A61B 17/7037 606/305 |
| 2006/0241596 A1* | 10/2006 | Rezach | A61B 17/7035 606/264 |
| 2006/0255521 A1* | 11/2006 | Brunner | A61B 17/645 269/86 |
| 2006/0271045 A1 | 11/2006 | Hubbard et al. | |
| 2006/0287652 A1* | 12/2006 | Lessig | A61B 17/645 606/54 |
| 2007/0038217 A1* | 2/2007 | Brown | A61B 17/6466 606/57 |
| 2007/0049932 A1* | 3/2007 | Richelsoph | A61B 17/645 606/252 |
| 2007/0106297 A1* | 5/2007 | Dumbauld | A61B 18/1445 606/51 |
| 2007/0173833 A1* | 7/2007 | Butler | A61B 17/7037 606/279 |
| 2007/0198012 A1* | 8/2007 | Thomke | A61B 17/60 606/54 |
| 2007/0233066 A1* | 10/2007 | Rezach | A61B 17/7037 606/252 |
| 2007/0293860 A1 | 12/2007 | Oesch et al. | |
| 2008/0065068 A1* | 3/2008 | Thomke | A61B 17/6466 606/57 |
| 2008/0194153 A1* | 8/2008 | De France | H01R 4/4872 439/822 |
| 2008/0215053 A1* | 9/2008 | Thomke | A61B 17/6466 606/59 |
| 2009/0036891 A1 | 2/2009 | Brown et al. | |
| 2009/0088751 A1* | 4/2009 | Mullaney | A61B 17/6466 606/59 |
| 2009/0254086 A1* | 10/2009 | Trilla-Muntanola | F16B 7/0433 606/54 |
| 2009/0299368 A1* | 12/2009 | Bauer | A61B 17/645 606/57 |
| 2009/0306661 A1* | 12/2009 | Thomke | A61B 17/645 606/54 |
| 2009/0326532 A1* | 12/2009 | Schulze | A61B 17/6441 606/56 |
| 2010/0204733 A1* | 8/2010 | Rathbun | A61B 17/88 606/251 |
| 2010/0262143 A1* | 10/2010 | Bordeaux | A61B 17/6466 606/54 |
| 2010/0298827 A1* | 11/2010 | Cremer | A61B 17/6466 606/54 |
| 2011/0066151 A1* | 3/2011 | Murner | A61B 17/6466 606/54 |
| 2011/0087226 A1* | 4/2011 | Murner | A61B 17/6466 606/54 |
| 2011/0098706 A1 | 4/2011 | Mullaney | |
| 2011/0098707 A1 | 4/2011 | Mullaney | |
| 2011/0112533 A1* | 5/2011 | Venturini | A61B 17/6466 606/54 |
| 2011/0172663 A1 | 7/2011 | Mullaney | |
| 2012/0004659 A1* | 1/2012 | Miller | A61B 17/6466 606/54 |
| 2012/0089142 A1* | 4/2012 | Mullaney | A61B 17/6466 606/54 |
| 2012/0095462 A1* | 4/2012 | Miller | A61B 17/6466 606/59 |
| 2012/0150182 A1* | 6/2012 | Dominik | A61B 17/6466 606/59 |
| 2012/0150184 A1* | 6/2012 | Mullaney | A61B 17/6466 606/59 |
| 2012/0150185 A1* | 6/2012 | Mullaney | A61B 17/6466 606/59 |
| 2012/0181054 A1* | 7/2012 | Melton | H02G 3/083 174/50 |
| 2012/0203225 A1* | 8/2012 | Mingozzi | A61B 17/6466 606/59 |
| 2012/0271356 A1* | 10/2012 | Ramsay | A61B 17/7032 606/278 |
| 2012/0296335 A1* | 11/2012 | Mullaney | A61B 17/6466 606/59 |
| 2016/0175011 A1 | 6/2016 | Mullaney | |

FOREIGN PATENT DOCUMENTS

| | | |
|---|---|---|
| CN | 103687558 B | 5/2016 |
| DE | 2430234 A1 | 1/1975 |
| EP | 1820461 A1 | 8/2007 |
| EP | 1922001 A2 | 5/2008 |
| EP | 2197372 A1 | 6/2010 |
| EP | 2294994 A1 | 3/2011 |
| JP | 2009504256 A | 2/2009 |
| JP | 2010540112 A | 12/2010 |
| JP | 2013530775 A | 8/2013 |
| JP | 2014521383 A | 8/2014 |
| WO | WO-8905126 A1 | 6/1989 |
| WO | WO-9011055 A1 | 10/1990 |
| WO | WO-9212683 A1 | 8/1992 |
| WO | WO-9851227 A1 | 11/1998 |
| WO | WO-9925264 A1 | 5/1999 |
| WO | WO-03065911 A1 | 8/2003 |
| WO | WO-2007021657 A2 | 2/2007 |
| WO | WO-2009004347 A1 | 1/2009 |
| WO | WO-2009042836 A1 | 4/2009 |
| WO | WO-2012158698 | 11/2012 |

OTHER PUBLICATIONS

"U.S. Appl. No. 13/471,998, Corrected Notice of Allowance dated Nov. 16, 2015", 2 pgs.

"U.S. Appl. No. 13/471,998, Examiner Interview Summary dated Apr. 18, 2014", 3 pgs.

"U.S. Appl. No. 13/471,998, Final Office Action dated Feb. 10, 2014", 18 pgs.

"U.S. Appl. No. 13/471,998, Non Final Office Action dated Apr. 23, 2015", 10 pgs.

"U.S. Appl. No. 13/471,998, Non Final Office Action dated Jun. 26, 2013", 15 pgs.

"U.S. Appl. No. 13/471,998, Notice of Allowance dated Oct. 20, 2015", 5 pgs.

"U.S. Appl. No. 13/471,998, Response filed Apr. 8, 2014 to Final Office Action dated Feb. 10, 2014", 10 pgs.

(56) References Cited

OTHER PUBLICATIONS

"U.S. Appl. No. 13/471,998, Response filed Jul. 7, 2015 to Non Final Office Action dated Apr. 23, 2015", 9 pgs.
"U.S. Appl. No. 13/471,998, Response filed Sep. 25, 2013 to Non Final Office Action dated Jun. 25, 2013", 12 pgs.
"U.S. Appl. No. 15/053,580, Corrected Notice of Allowability dated Nov. 8, 2017", 2 pgs.
"U.S. Appl. No. 15/053,580, Non Final Office Action dated Apr. 20, 2017", 12 pgs.
"U.S. Appl. No. 15/053,580, Notice of Allowance dated Oct. 2, 2017", 5 pgs.
"U.S. Appl. No. 15/053,580, Response filed Jun. 8, 2017 to Non Final Office Action dated Apr. 20, 2017", 10 pgs.
"U.S. Appl. No. 15/053,580, Preliminary Amendment filed Apr. 14, 2016", 9 pgs.
"Chinese Application Serial No. 201280035461.1, Office Action dated Jul. 1, 2015", (W/ English Translation), 9 pgs.
"Chinese Application Serial No. 201280035461.1, Voluntary Amendment filed Jul. 11, 2014", (w/English Claims), 10 pgs.
"European Application Serial No. 12722655.3, Communication Pursuant to Article 94(3) EPC dated Nov. 29, 2016", 5 pgs.
"European Application Serial No. 12722655.3, Response filed May 25, 2017 to Communication Pursuant to Article 94(3) EPC dated Nov. 29, 2016", 20 pgs.
"International Application Serial No. PCT/US2008/077800, International Search Report dated Dec. 2, 2008", 4 pgs.
"International Application Serial No. PCT/US2008/077800, Written Opinion dated Dec. 2, 2008", 5 pgs.
"International Application Serial No. PCT/US2011/042813, International Search Report dated Oct. 13, 2011", 4 pgs.
"International Application Serial No. PCT/US2011/042813, Written Opinion dated Oct. 13, 2011", 5 pgs.
"International Application Serial No. PCT/US2011/055907, International Search Report dated Jan. 9, 2012", 3 pgs.
"International Application Serial No. PCT/US2011/055907, Written Opinion dated Jan. 9, 2012", 5 pgs.
"International Application Serial No. PCT/US2011/059303, International Search Report dated Mar. 20, 2012", 5 pgs.
"International Application Serial No. PCT/US2011/059303, Written Opinion dated Mar. 20, 2012", 7 pgs.
"International Application Serial No. PCT/US2011/063976, International Search Report dated Apr. 10, 2012", 3 pgs.
"International Application Serial No. PCT/US2011/063976, Written Opinion dated Apr. 10, 2012", 3 pgs.
"International Application Serial No. PCT/US2011/063985, International Search Report dated Mar. 28, 2012", 4 pgs.
"International Application Serial No. PCT/US2011/063985, Written Opinion dated Mar. 28, 2012", 4 pgs.
"International Application Serial No. PCT/US2012/037957, International Preliminary Report on Patentability dated Nov. 28, 2013", 11 pgs.
"International Application Serial No. PCT/US2012/037957, International Search Report dated Oct. 4, 2012", 6 pgs.
"International Application Serial No. PCT/US2012/037957, Written Opinion dated Oct. 4, 2012", 9 pgs.
"Japanese Application Serial No. 2014-511456, Office Action dated Sep. 20, 2016", (With English Translation), 5 pgs.
"Japanese Application Serial No. 2014-511456, Response filed Jun. 21, 2016 to Notice of Reasons for Rejection dated Mar. 22, 2016", (W/ English Translation), 11 pgs.
"Japanese Application Serial No. 2014-511456, Notice of Reasons for Rejection dated Mar. 22, 2016", (W/ English Translation), 11 pgs.
"Japanese Application Serial No. 2014-511456, Response filed Nov. 28, 2016 to Office Action dated Sep. 20, 2016", (W/ English Translation), 9 pgs.
"Swiss Application Serial No. 03891906, Application filed Dec. 16, 1991", Swiss Patent Office, "Fixateur exteme," Applicant—Jaquet Orthopedie S.A., (No English Translation), (Dec. 16, 1991), 34 pgs.

* cited by examiner

EXTERNAL FIXATION CLAMP USING A TRIGGER MECHANISM AND STORED SPRING ENERGY

PRIORITY

This application is a continuation of U.S. patent application Ser. No. 15/053,580, filed on Feb. 25, 2016, which is a continuation of U.S. patent application Ser. No. 13/471,998, filed on May 15, 2012, which claims the benefit of priority to U.S. Provisional Patent Application Ser. No. 61/487,154, filed on May 17, 2011, which applications are incorporated herein by reference in their entireties.

FIELD OF THE INVENTION

This disclosure is directed to an external fixation clamping system utilizing a trigger mechanism, and more particularly, this disclosure is directed to an external fixation clamping system with stored spring energy.

BACKGROUND

External fixation systems are used to stabilize fractured bones or to secure bones after corrective surgery. They are usually made up of structural members held together by clamps, all assembled by the surgeon during surgery. The clamps are placed on bone pins and are attached to bars, creating a frame to hold the bones in particular relationships. Typically, the external fixation frame is assembled in the configuration the surgeon desires, then the fracture is reduced and the clamps are tightened. Some conventional clamps have to be tightened partially to provisionally lock the bone pin or bar into the clamp.

In one known external fixation clamping apparatus, the fixation element is inserted against an axial spring force that forces the outer and inner jaws together. The same spring provides a provisional locking force that retains the fixation element prior to final clamping. The force of the spring is dependent on the degree to which a nut is threaded into the clamping apparatus. In the fully unthreaded state, the force is relatively low and the fixation element can be inserted rather easily. It can pop out rather easily as well. As the nut is progressively threaded into the clamping apparatus, this spring force becomes greater and at some point the clamping apparatus is threaded to such a degree that the insertion of a fixation element is mechanically prohibited. The point at which this occurs also varies based on whether the fixation element is the first or the second element to be inserted into the clamping apparatus. It is therefore possible to find that after insertion of the first fixation element, the insertion of the second fixation element requires that the clamping apparatus be loosened. This variability is, at a minimum, a nuisance. In other known devices, the spring force acts on a latch slide that must be forced open by the act of inserting the fixation element. The spring element acted on during the act of insertion only provides a return force on the latch device once the fixation element is inserted; it does not provide any provisional clamping force and so the fixation element, while retained, is loose in the clamp prior to tightening the clamping element, This too is, at a minimum, a nuisance.

SUMMARY

In one aspect, the present disclosure is directed to an external fixation clamp for receiving a fixation element. The clamp includes an inner jaw and an outer jaw cooperatively arranged with the inner jaw to capture a fixation element. The inner and outer jaws may be movable between an open position that permits the fixation element to be placed between the inner and outer jaws and a closed position that restricts removal of the fixation element from between the inner and outer jaws. A latch assembly may cooperate with the inner and outer jaws to secure the jaws in a closed position. The latch assembly may comprise a latch and a latch biasing member. The latch may be configured to translate linearly relative to one of the inner and outer jaws, and the latch biasing member may have a first higher level of stored energy when the inner and outer jaws are in the open position and a second lower level of stored energy when the inner and outer jaws are in the closed position.

In one aspect, the change in stored energy is a result of un-compressing the latch biasing member element during the linear translation of the latch.

In one exemplary aspect of the present disclosure an external fixation clamp for receiving a fixation element includes an inner jaw having a first seat for a first fixation element having a first size and having a second seat for a second fixation element having a second size different than the first size. An outer jaw may be cooperatively disposed to capture a fixation element. The outer jaw having a third seat for the first fixation element of the first size and a fourth seat for the second fixation element of the second size. In one aspect, one of the first seat and the third seat is a transverse groove.

In one exemplary aspect, the present disclosure is directed to an external fixation clamp for receiving a fixation element. The clamp may include an inner jaw and an outer jaw cooperatively arranged with the inner jaw to capture a fixation element. The inner and outer jaws may be movable between an open position that permits the fixation element to be placed between the inner and outer jaws and a closed position that restricts removal of the fixation element from between the inner and outer jaws. A biasing element is disposed between the first and second jaws and configured to bias the first and second jaws to the open position. In one aspect, the biasing element is disposed to apply loading against a projecting tab on the outer that biases the outer jaw toward the open position.

In one exemplary aspect, the present disclosure is directed to an external fixation clamp for receiving a fixation element. The clamp may include an inner jaw and an outer jaw cooperatively arranged with the inner jaw to capture a fixation element. A latch assembly may be cooperatively arranged with the inner and outer jaws to trigger and release energy stored within the clamp upon displacement of one of the inner and outer jaws as a result of contact with the fixation element.

In one exemplary aspect, the present disclosure is directed to a method including inserting a fixation element against a portion of the first jaw so that the first jaw rotates relative to the second jaw and compresses a jaw biasing element biasing the fixation element; and releasing energy from a latch biasing element as a latch moves toward the fixation element so that overall potential energy is reduced.

BRIEF DESCRIPTION OF THE DRAWINGS

Aspects of the present disclosure are best understood from the following detailed description when read with the accompanying figures.

DETAILED DESCRIPTION

Figure 1:
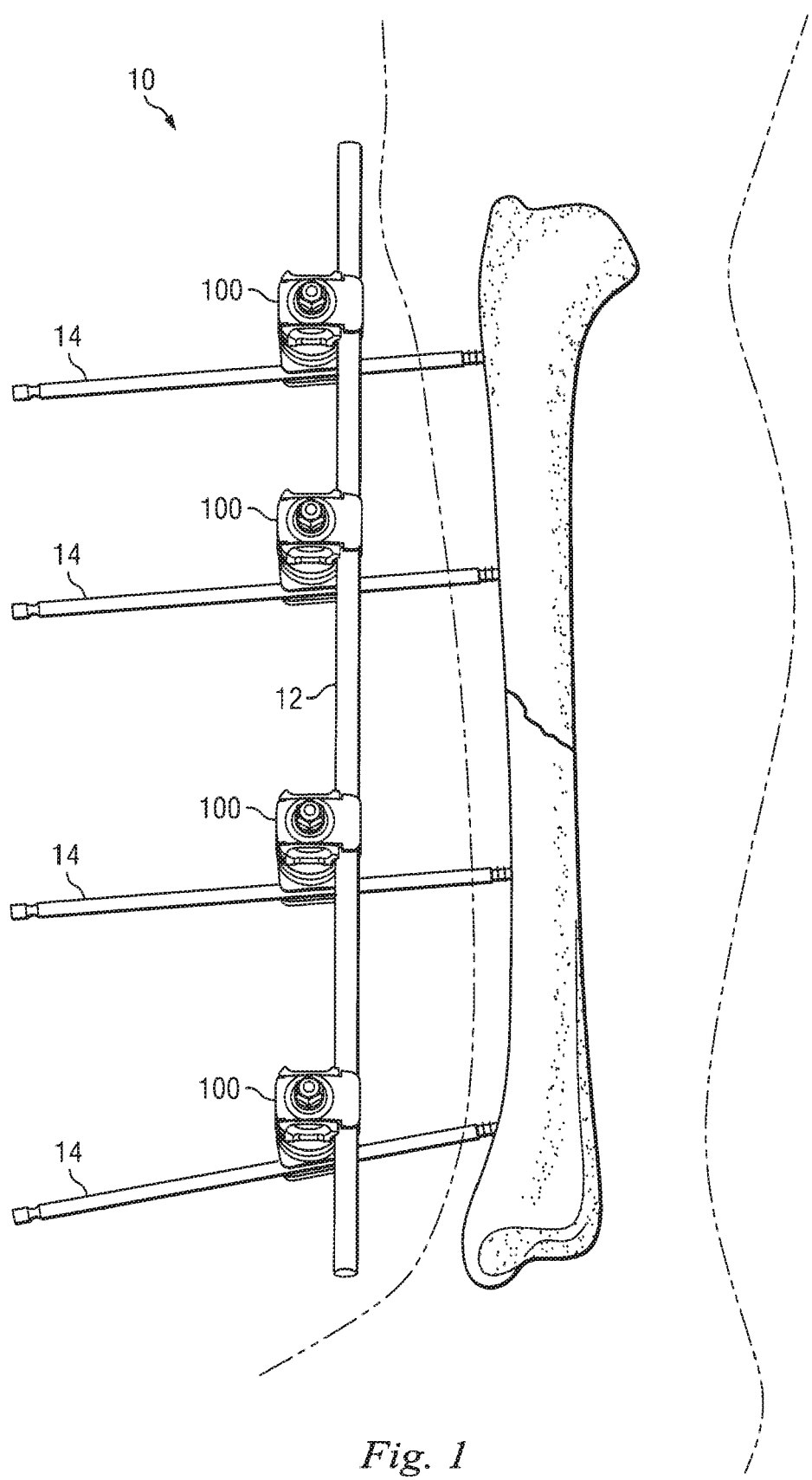
FIG. 1 is an illustration of an exemplary external fixation system in accordance with one exemplary aspect of the present disclosure connected to a patient's bone tissue.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present disclosure is directed to an external fixation system with a clamping assembly that employs a triggering and cocking-type system that stores a higher level of spring energy before a fixation device is inserted into a clamp than after the fixation element is inserted into the clamp.

In one aspect, the present disclosure is directed to an external fixation system with a clamping assembly, where the clamping action is consistent and not dependent on the position of a tightening nut. In another aspect, a spring force can be preloaded by a "cocking action" such that the act of inserting the fixation element simply triggers the closure of the jaws, and which then provides a provisional load on and positive retention of the fixation element. Such a system as described can be characterized and differentiated from prior systems by a fundamental aspect of the design, namely stored energy.

In one aspect, this disclosure is directed to a clamping device for an external fixation system that is pre-configured with a higher degree of stored energy prior to insertion of a fixation element, whereby that stored energy is released by a trigger whose action is the result of the insertion process on the part of the fixation element, resulting in a lower amount of stored energy when the fixation element was in the clamp mechanism. Accordingly, the stored energy decreases by insertion of the fixation element into the clamp. In addition, a predictable amount of the energy released during insertion of the fixation element may be utilized as potential energy present as a force acting on the fixation element to thereby provide a provisional clamping load.

In addition, one aspect of the present disclosure separates the latching and provisional loading functions from the clamping function. This provides several advantages over prior designs. For example, the clamping assembly disclosed herein may provide a design whose clamping function requires minimal travel, lessening the amount of turns required by a locking nut to go from completely loose to completely clamped, which saves time when considering that many such clamping elements must be tightened. In addition, the clamping assembly may include a design whose ability to accept a fixation element is not dependent on the position of the clamping element and so one need not adjust the clamping element to the proper location in order that a fixation element is able to be inserted. Further, the clamping assembly may include a design that can be set to accept a fixation element with a simple quick pull back of a slide, much like cocking a gun, requiring no tools, no twisting, no trial and error, etc. The clamping assembly may also include a design where the ability of which to accept a fixation element is not dependent on whether or not it is the first or second element to be placed. In another aspect, the clamping assembly may include a design whereby the action of removal of a fixation element places the clamp is a state ready to accept a fixation element.

In another exemplary aspect, the present disclosure is directed to an external fixation clamp for receiving a fixation element. The clamp includes an inner jaw and an outer jaw cooperatively arranged with the inner jaw to capture a fixation element. It also includes a latch assembly cooperatively arranged with the inner and outer jaws to trigger and release energy stored within the clamp upon displacement of one of the inner and outer jaws as a result of contact with the fixation element.

FIG. 1 shows an exemplary external fixation system 10 attached to a patient's fractured tibia. The system 10 includes fixation elements as one or more rigid bars 12 extending between clamping devices 100 and includes one or more pins 14 drilled into the bone on opposing sides of the fracture. Although this disclosure references bars and pins, it should be understood that any fixation element may be used, including bone pins, wires, rings, struts, bars, rods, or other structural members. In the example in FIG. 1, each pin 14 is received into one of the clamping devices 100 by inserting the pin 14 between facing jaws of a pin clamp of the clamping device 100. Likewise, the bar 12 is received into each of the clamping devices 100 by inserting the bar 12 between facing jaws of a bar clamp of each clamping device 100 as is described further below, to establish the external fixation framework for bone stabilization. In some embodiments, inserting the bar 12 or pin 14 triggers the clamp to place it in a provisionally locked condition. In this position, the respective clamp can be rotated about the bar 12 or pin 14 and may be axially displaced along the bar 12 or pin 14. In addition, at least one of the clamps may rotate about a longitudinal axis of the clamping device 100, and may pitch up or down around the cylindrical axis of a saddle element, while the jaws maintain the bar or pin in the clamp. As remaining pins 14 are connected to the bar 12 using one of the clamping devices 100, the clamps may be adjusted to provide angulations and orientation necessary to align the bone for healing. Additional bar-to-bar fixation clamps and/or bar-to-pin fixation clamps may be added to expand and connect the frame as required. Some embodiments include multi-pin clamps. Once properly created, the frame may be locked by changing the clamp from a provisionally locked condition to the locked condition.

Figure 2:
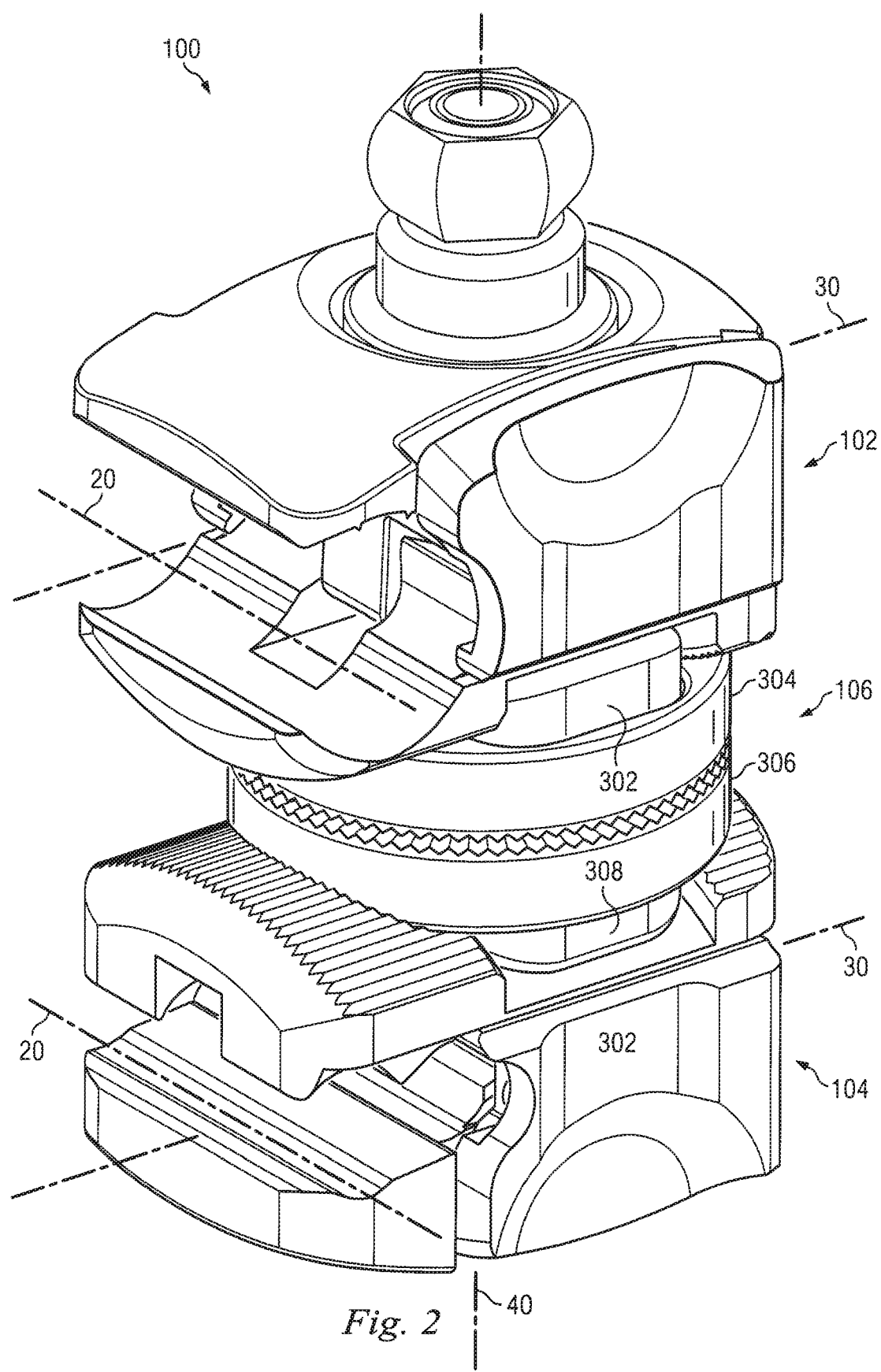
FIG. 2 is an illustration of a clamping assembly of an external fixation system according to one exemplary aspect of the present disclosure.
Figure 3:
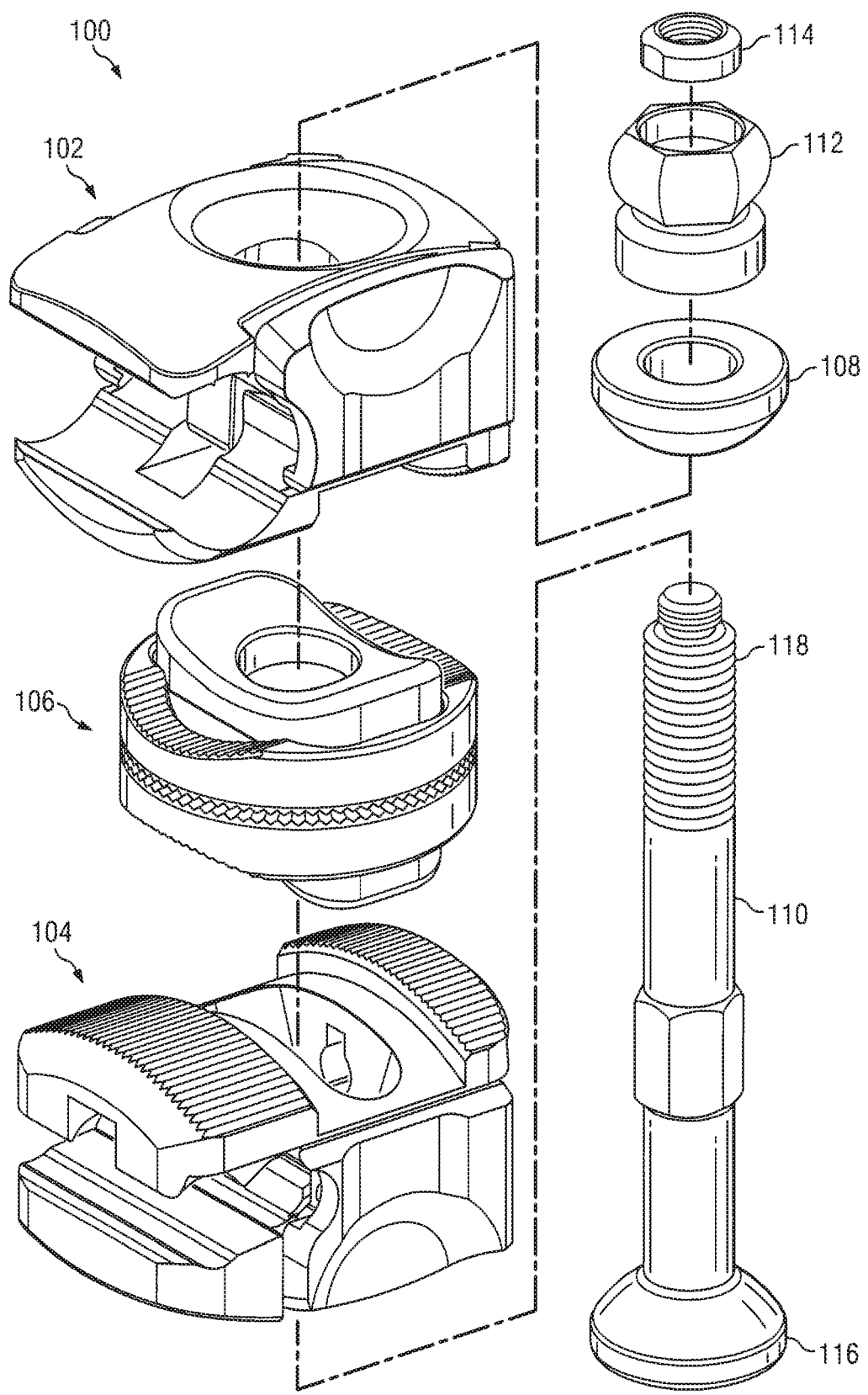
FIG. 3 is an illustration of the clamping assembly of FIG. 2 in a partially exploded configuration according to one aspect of the present disclosure.

FIGS. 2-22 show an exemplary embodiment of the clamping device 100. FIG. 2 shows an isometric view of the clamping device and FIG. 3 shows a partially exploded view of the clamping device 100. The exemplary clamping device 100 includes a rod clamp 102, a pin clamp 104, and a base assembly or saddle assembly 106 disposed there between. Each clamp 102, 104 independently receives and secures a bar, pin or other fixation element. Other embodiments of the clamping device 100 include two rod clamps or two pin clamps. Yet other embodiments include only a single clamp on one end, with a multi-clamp set or other arrangement on the other end.

Each clamp 102, 104 of the clamping device 100 provides multiple degrees of freedom, each operating independently of the other. FIG. 2 shows the degrees of freedom as a roll axis 20, a pitch axis 30, and a yaw axis 40 in the upper and lower clamps 102, 104. The roll axis 20 is the axis of a fixation element within the clamps and about which the clamping device 100 may rotate when the clamp is only provisionally locked. The pitch axis 30 is the axis about which the outer and inner jaws rotate relative to the saddle assembly 106 and relative to the opposing clamp. The yaw axis 40 is defined by a post (described below) and about which one of the clamps 102, 104 can rotate relative to the other.

As described in greater detail below, the rod and pin clamps 102, 104 are, for the most part, similar, with the pin clamp 104 configured in this embodiment to accept a pin of any of a plurality of sizes. In one example, the pin clamp 104 is configured to accept both a 5 mm or a 6 mm fixation element while the rod clamp 102 is so configured to accept an 11 mm fixation element. In other embodiments, however, the pin clamp 104 is configured to accept a 4 mm or a 6 mm fixation element. Other embodiments accept fixation elements of other sizes. The rod clamp 102 may also be dimensioned to accept a suitable sized rod, whether larger or smaller than the example of 11 mm provided above.

In this embodiment, the saddle assembly 106 is a self contained subassembly comprised of biasing or spring washers, inter-digitations and bearing components, along with a retention device that act together to provide a tailored degree of friction up to and including a positive locking of rod and pin clamps 102, 104 with regard to the degrees of freedom. As used herein, the front or forward end of the clamps 102, 104 is the side of the clamp that receives the fixation element and the rearward or backside is the side opposite the side of the clamp receiving the fixation element.

FIG. 3 shows a partially exploded view of the clamping device 100. In addition to the rod clamp 102, the pin clamp 104, and the saddle assembly 106, the clamping device 100 includes a locking subassembly comprising a spherical washer 108, a post 110, a nut 112, and a lock nut 114 that serves as a retention device to prevent inadvertent disassembly. In the example shown in FIG. 3, the post 110 includes a spherical head 116 on one end and threads 118 at the other end that acts along with spherical washer 108 and nut 112 to provide the locking function. The lock nut 114, in this example, has threads opposite that of the threads 118 and is threaded onto the post 110 to ensure that nut 112 cannot be removed inadvertently. In this example, the lock nut thread is a left hand thread that ensures that when nut 112 is backed-up against the lock nut 114, the act of further loosening the nut 112 will act to tighten lock nut 114. In some embodiments, lock nut 114 is further secured with the use of a locking compound. The spherical head 116 of the post 110 and the spherical washer 108 ensure that mobility and self alignment is maintained between the pin clamp 104 and the rod clamp 102 during the clamping action. The post 110 has a hexagonal form mid shaft to mate with a non-circular spacer (described with reference to FIG. 19) to provide an anti-rotation feature such that when the nut 112 is tightened, the post 110 does not simply spin within the rod and pin clamps.

In the example shown, the nut 112 is selected to be rotationally engaged adjacent the rod clamp 102 instead of the pin clamp 104. This enables torque reaction loads to be carried by the thicker rod fixation element 12 (such as an 11 mm bar for example,) rather than the thinner fixation elements 14 (such as 5 or 6 mm pins for example). In addition, when the pin clamp 104 and the rod clamp 102 are rotated relative to one another about the post 110, the post 110 and the nut 112 rotate together such that no loosening or tightening occurs. This is a very important benefit to the surgeon over conventional systems, as it prevents a premature lock up or an inadvertent loosening of the clamping assembly 100 during the reduction of the facture while maintaining the degree of tightening that the surgeon would like. In other embodiments, the post is inverted so that the nut 112 is rotationally engaged adjacent the pin clamp 104. In some embodiments, the post component does not include a head, but has two threaded ends that cooperate with two nuts for tightening the clamping assembly 100. Additional description of the axes and a post component or stud can be found in U.S. patent application Ser. No. 13/271,744 to Mullaney, filed Oct. 12, 2011, incorporated herein by reference. In this example, the nut 112 also has an additional feature that is of benefit to the surgeon, namely a ball formed hex as opposed to a more conventional straight hexagonal form. This allows the placement of a socket driver (not shown) to within a conical volume rather than needing to be coaxial with the nut, Essentially this provides a universal joint of sorts that increases the user friendliness of the clamping assembly 100.

Figure 4:
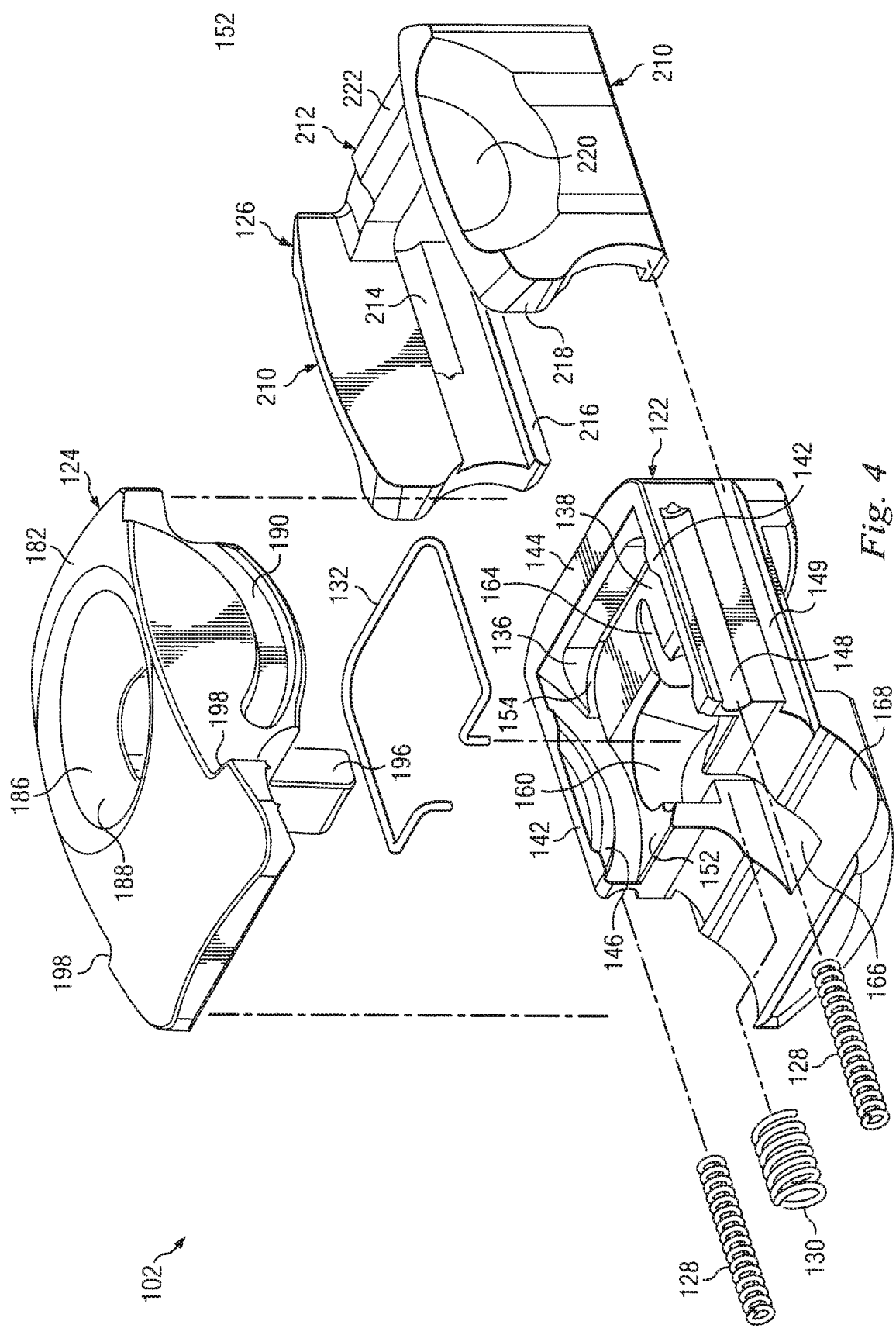
FIG. 4 is an illustration of an exploded isometric view of a clamp of the clamping assembly of FIG. 2 in accordance with one exemplary aspect of the present disclosure.
Figure 5:
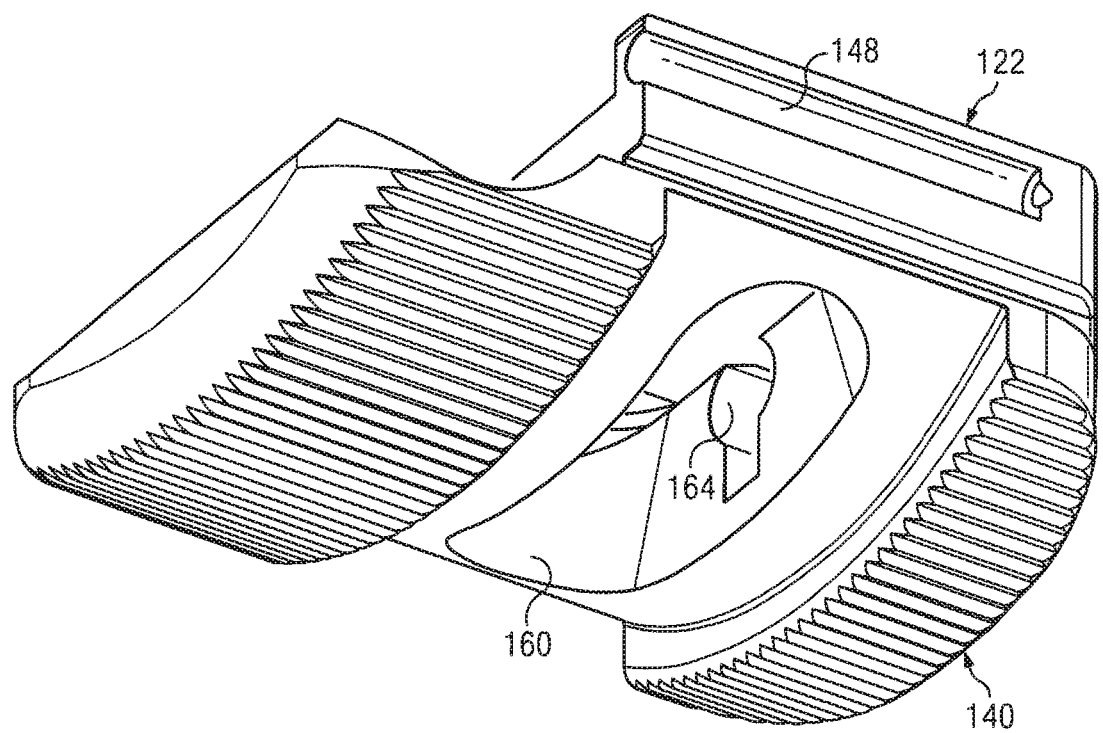
FIG. 5 is an illustration of an inner jaw of the clamp of FIG. 4 according to one aspect of the present disclosure.
Figure 6:
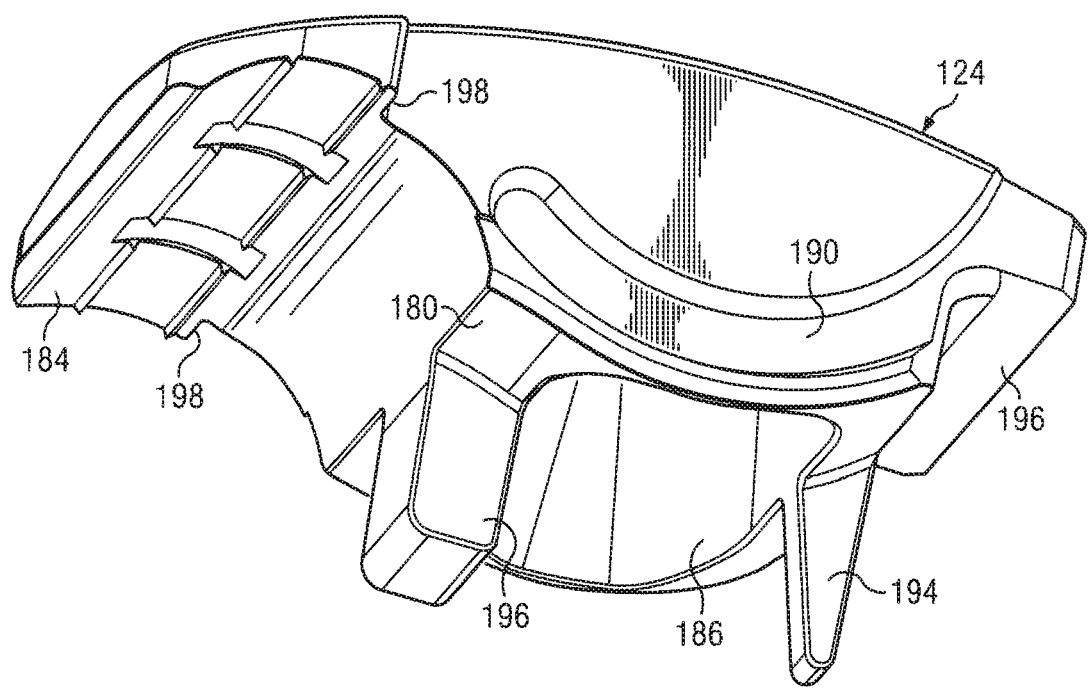
FIG. 6 is an illustration of an outer jaw of the clamp of FIG. 4 according to one aspect of the present disclosure.
Figure 7:
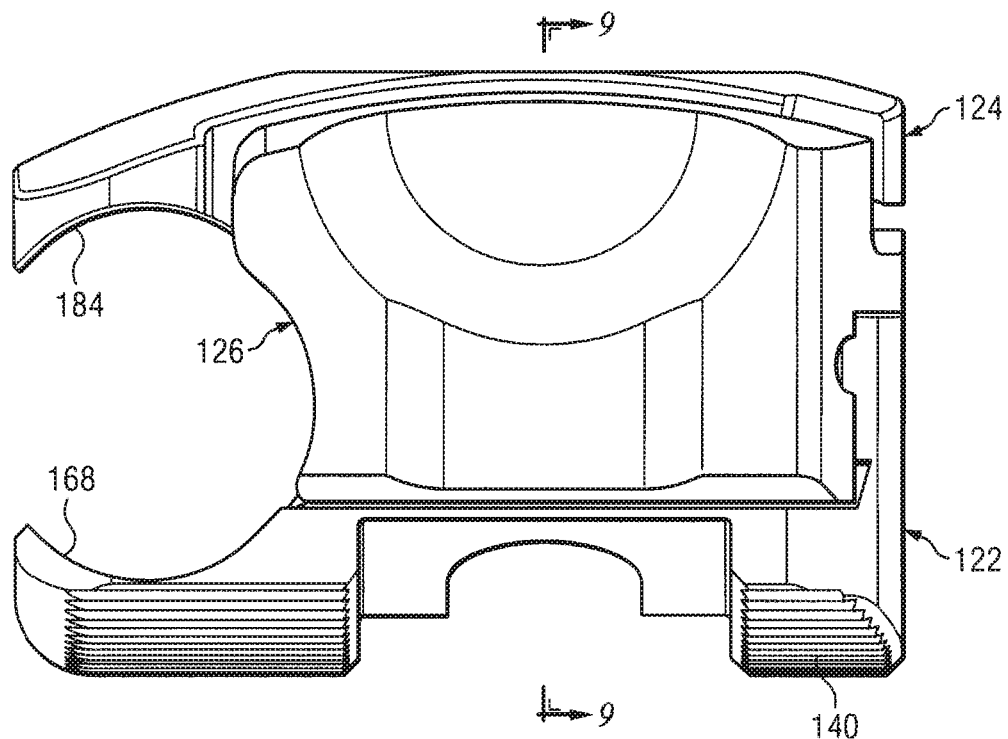
FIG. 7 is an illustration of the clamp of FIG. 4 showing a side view according to one aspect of the present disclosure.
Figure 8:
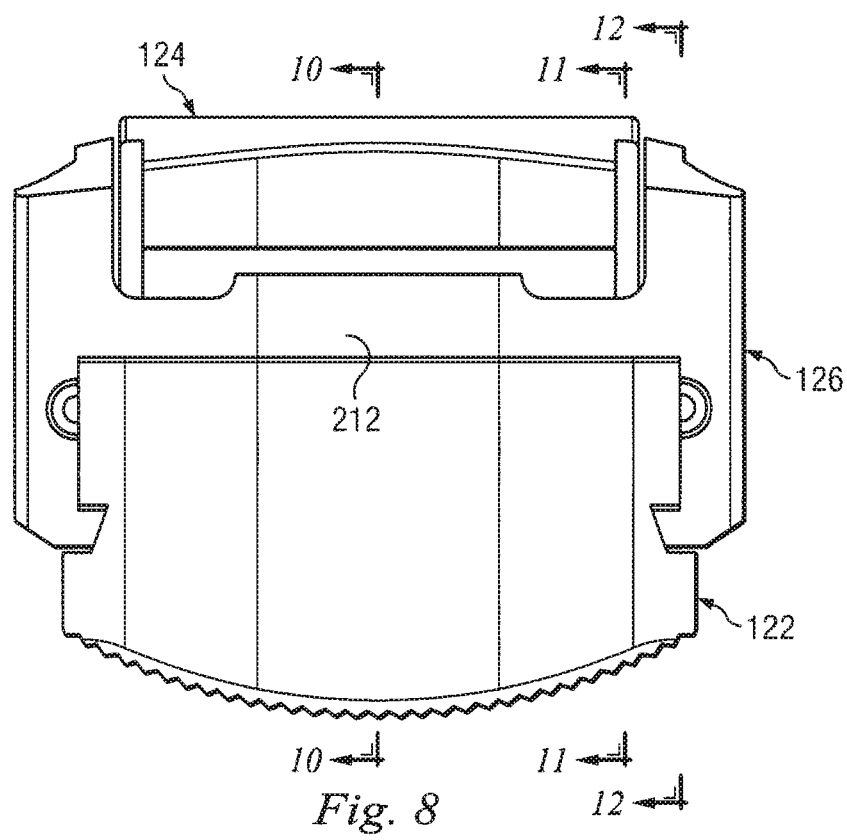
FIG. 8 is an illustration of the clamp of FIG. 4 showing a back or rearward view according one aspect of the present disclosure.

The rod clamp 102 is described in greater detail with reference to FIGS. 4-12. FIG. 4 shows an exploded view, FIGS. 5 and 6 shows respectively inner and outer jaws, FIG. 7 shows a side view, FIG. 8 shows a back view, and FIGS. 9-12 show cross-sectional views.

The rod clamp 102 includes an inner jaw 122, an outer jaw 124, a latch 126, and a plurality of biasing members. These are identified as one or more latch biasing members or latch springs 128, one or more jaw biasing members or jaw springs 130, and one or more clamp biasing members shown as one or more spring wires 132.

In this embodiment, the inner jaw 122 includes a body with a hollow center or recess 136 arranged to receive a portion of the outer jaw 124. The inner jaw 122 cooperates with the outer jaw 124 to clamp onto and secure a fixation element. It includes an inner clamp face 138 that faces toward the outer jaw 124 and includes an outer clamp face 140 (see FIG. 5) that faces and interfaces with the saddle assembly 106 (FIG. 3). Because of its hollow construct, the inner jaw 122 also includes side wall portions 142 and a rear wall portion 144. The side wall portions 142 include an inner facing portion having a projecting guide 146 formed thereon. In FIG. 4, the projecting guide 146 is shown as a projecting arc. Along an outer facing portion of the sidewall portions 142 or along the side of the inner jaw are a latch spring seat 148 and a notch 149. The latch spring seats 148 are shown as grooves extending along a side from a forward end of the inner jaw 122 toward the rearward end. The latch spring seats 148 are open at the front end and closed at the rearward end and cooperate with the latch springs 128 to bias the latch 126. The notch 149 is disposed below the latch spring seats 148 and is configured to receive and associate with a portion of the latch 126.

The inner clamp face 138 includes a concavity or depression 152 formed therein. In addition, the inner clamp 122 includes receiving portions 154 in the corners of the hollow center or recess 136 that receive and support corresponding corners of the spring wire 132. As will be described in greater detail below, the receiving portions 154 support the corners of the spring wire 132, while the shape of the depression or concavity 152 permits the spring wire 132 to deflect downwardly into the concavity under loading. This will be described further below.

A central bore 160 extends from the inner clamp face 138 to the outer clamp face 140 and is sized to receive the post 110. The clamp may turn about the post providing rotation about the yaw axis 140 (FIG. 3). In the example shown, the central bore 160 is configured to permit the rod clamp 102 to rotate about the pitch axis relative to the post in the manner shown in FIG. 2. Accordingly, the central bore 160 is formed with a length and a width, that length being greater than the width. The central bore 160 is shown in cross-section in the views of FIGS. 9 and 10. The central bore 140 is described in greater detail in U.S. patent application Ser. No. 13/271,744 to Mullaney, filed Oct. 12, 2011 (published as U.S. Patent Publication No. 2012/0089142), incorporated herein by reference.

A partial cylindrical bore 164 formed in the inner clamp face 138 extends from the central bore 160 toward the rear of the inner jaw 122. The partial cylindrical bore 164 is sized to house the jaw spring 130 and to receive a downwardly extending portion of the outer jaw 124 in a manner that will be described below. In the example shown the partial cylindrical bore 164 is sized and shaped with an upper opening smaller than the maximum width of the groove, such that the partial cylindrical bore 164 may house the jaw spring 130, but the jaw spring 130 may not exit the partial cylindrical bore 164 through the inner clamp face 138. Instead, in this example the jaw spring 130 may be placed into or removed from the partial cylindrical bore 164 at the intersection of the partial cylindrical bore 164 and the central bore 160. A trigger groove 166 extends from the central bore 160 toward the forward end of the inner jaw 122. This trigger groove 166 accommodates a portion of the outer jaw 120 that will be described below.

The outer clamp face 140 is a semi-cylindrical shaped surface that includes parallel, longitudinal splines shown in FIG. 5. These are configured to interdigitate with the corresponding splines on the saddle assembly 106. The cylindrical shaped surface defines a radius about which the inner jaw 122 pivots to provide the range of motion. Although splines are shown in FIG. 5, some examples use other friction enhancing features, such as roughened surfaces, knurls, or even smooth surfaces that can sufficiently engage to reduce the likelihood of relative pivoting when desired.

The inner jaw 122 also includes a fixation element gripping surface portion 168 shown as a transverse groove (FIG. 4). The gripping surface portion 168 is disposed at the forward or gipping side of the clamp 102 and engages the fixation element or rod 12. It extends from one lateral side to another and is shaped to receive a bar, pin, or other fixation or stabilization component. The gripping surface portion 168 is formed with a hook or lip at the front end of the clamp that secures the fixation element in the clamp. The gripping surface portion 168 may be formed with a rounded bottom portion or may be formed of a series of flats or faces. Some embodiments may have a combination of both curves and flats. The depth of the gripping surface portion 168 may vary between different clamps depending on the size of the fixation element intended to be gripped by the clamp. In some embodiments, the configuration and depth of the gripping surface portion 168 may be configured to secure a smaller diameter bar, such as a bone pin or may be configured to secure a larger diameter bar, such as a frame bar. Further, in some embodiments, because the cross-section of the bars and pins may have shapes other than circular, the gripping surface portion 168 may be shaped to also mateingly interface with these bars and pins. For example, the gripping surface portion 168 may include teeth, cut-outs, or other features that interface with bars having a non-smooth or non-circular outer surface.

The outer jaw 124 includes an inner clamp face 180 (FIG. 6) and an outer clamp face 182 (FIG. 4). The inner clamp face 180 includes a bar-receiving transverse gripping surface portion 184, and a central bore 186. Similar to the gripping surface portion 168 on the inner jaw 122 described above, the gripping surface portion 184 extends from one lateral side to another and is shaped to cooperate with the inner jaw 108 to receive a bar, pin or other fixation or stabilization component. Like the gripping surface portion 168 discussed above, the gripping surface portion 184 may be formed with a rounded bottom portion, flats, faces, or some combination of those. In some embodiments, the depth and shape of the gripping surface portion 184 is the same as the depth and shape of the gripping surface portion 168. Accordingly, the discussion above relating to the gripping surface portion 168 is equally applicable to the gripping surface portion 184. In this example, the gripping surface portion 184 includes laterally extending teeth and includes relies that may improve fixation.

Figure 9:
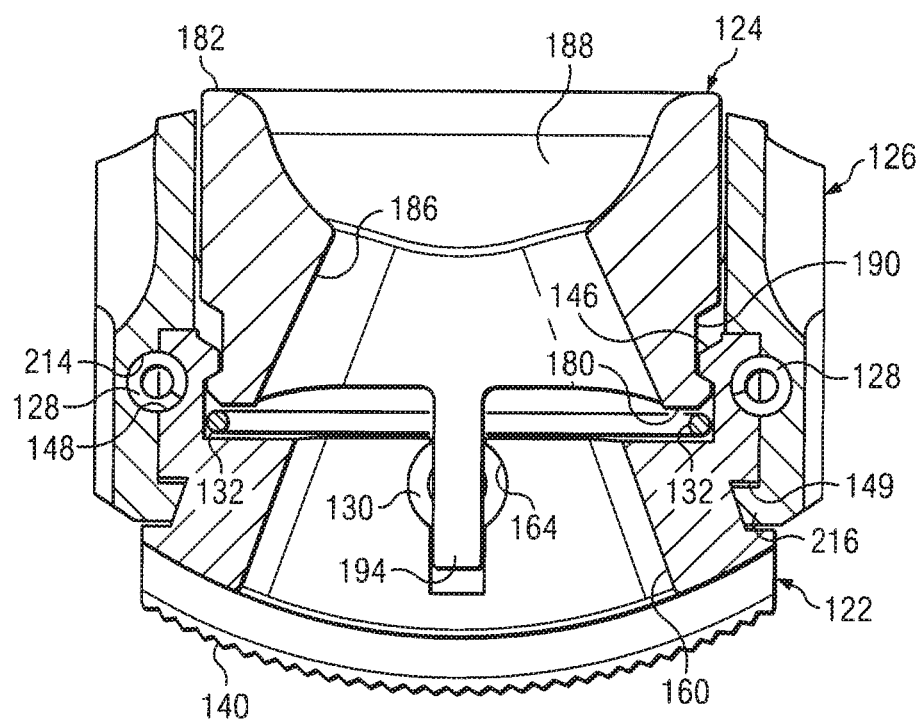
FIG. 9 is an illustration of a cross-section of the clamp of FIG. 7 taken through the lines 9-9 in FIG. 7 according to one exemplary aspect of the present disclosure.

The central bore 186 includes features that enable it to provide articulation relative to the post 110 in a manner that the outer jaw articulation matches that of the inner jaw 122. In some examples, and as can be seen in the cross-sectional views of FIGS. 9 and 10, the central bore 186 is generally hour-glass shaped, with a narrowing neck located between the inner clamp face 180 and the outer clamp face 182. At the inner clamp face 180, the central bore 186 is relatively rectangular shaped with a width and a length, the length being greater than the width. From the inner clamp face 180, the bore tapers inwardly toward the neck, with the inner bore surfaces including curved portions as well as planar portions. In the embodiment shown, and as best seen in FIG. 9, the central bore 186 is sized to permit pivot rotation in the lateral direction of the outer jaw 124 within, for example, a pivot range of 40 degrees, matching that of the inner jaw 122. Other pivot ranges are contemplated and considered to be within the scope of this disclosure. The pivot range may be modified by changing the size of the bores 160, 186. Unlike the exemplary inner jaw 122, however, the outer jaw 124 in this embodiment is configured to also provide articulation in the longitudinal direction or front-to-rear direction as can be seen by the angles shown in the cross-section of FIG. 10.

The portion of the central bore 186 adjacent the outer clamp face 182 is shaped as a spherical pocket 188. The spherical pocket 188 is configured to receive and articulate about the spherical washer 108, or alternatively, depending on the assembly, the spherical head 116.

The outer jaw 124 includes lateral sides having a track 190 formed therein. The track 190 is sized and configured to receive the projecting guide 146 on the inner jaw 122. This can be seen in FIGS. 9 and 11. In the example shown, the track 190 is shaped in an arc that permits the outer jaw 124 to slide along the projecting guide 146 relative to the inner jaw 122. In addition the track 190 has a track width that is greater than the width of the projecting guide 146. Accordingly, the outer jaw 124 is able to displace axially along the post 110 relative to the inner jaw 122 even while the projecting guide 146 is disposed within the track 190. This can be seen best in the clearance in FIG. 9. In this embodiment, the track 190 is also shaped concentrically with the spherical pocket 188 so that when the outer jaw 124 rotates about the track 190, it also rotates about the spherical washer 108 or head 116.

Projecting from the inner clamp face 180 are a pivot tab 194 and a loading pin 196. The pivot tab 194 is disposed rearward of the central bore 186 and configured to fit within the partial cylindrical bore 164 of the inner jaw 122. The loading pin 196 is disposed forward of the central bore 186 and is configured to be engaged by a fixation element, such as a rod being inserted into the clamp 102. It is configured to fit within the loading pin groove 166. The loading pin 196 acts as a surface on which the fixation element acts to trigger the closure of the clamp.

Adjacent the gripping surface portion 184, the outer clamp 124 comprises shoulders 198 (FIG. 4) having a width larger than the hollow recess 136 of the inner jaw 122. These shoulders 198 may limit the forward movement of the latch 126. The rearward end of the outer jaw 124 includes a stop surface 196 that is sized and arranged to fit about the latch when the latch is in the locked position as shown in the cross-sectional view in FIG. 10. This stop surface 196 abuts the latch and prevents the clamp from opening after the upper jaw 124 rotates along the track 190 and enters a locked position.

In other embodiments, the projecting guide 146 is formed on the outer jaw and the track 190 is formed on the inner jaw. In other embodiments, the projecting guide is disposed on an outwardly facing surface of the side wall portions 142 and the track is formed on the outer jaw. Other arrangements are also contemplated.

The latch 126 is described with reference to FIG. 4. The latch 126 includes two sidewalls 210 connected by a rear bar 212. The sidewalls 210 include an inner facing surface portion having a partial cylindrical bore 214 and a protruding lip 216 formed therein. The partial cylindrical bore 214 is configured to align with the partial cylindrical bore 164 on the inner jaw 122. On the latch 126 however, the partial cylindrical bore 214 extends from the rearward end toward the forward end of the latch 126. The partial cylindrical bore 214 on the latch 126 and the partial cylindrical bore 164 on the inner jaw 122 cooperate to retain the latch springs 128. This is best seen in the cross-sectional view in FIG. 12. Because of the oppositely disposed closed ends of the partial cylindrical bores, the latch springs 128 bias the latch 126 toward the front of the clamp 102. The protruding lip 216 is sized to fit within the notch 149 (FIG. 9) and secure the latch 126 to the inner jaw 122. Accordingly, the latch 126 may slide forward and rearward along the inner jaw 122. A leading end 218 of the sidewalls 210 is configured to abut against the shoulder 198 of the outer jaw 124. Alternatively, a leading surface of the sidewalls may abut directly against a fixation element in the clamp 102. The outer surfaces of the sidewalls 210 include finger gripping surfaces 220 that enable a user to grasp the latch 126 to pull it in the rearward direction to open the clamp 102 as will be described below.

Figure 10:
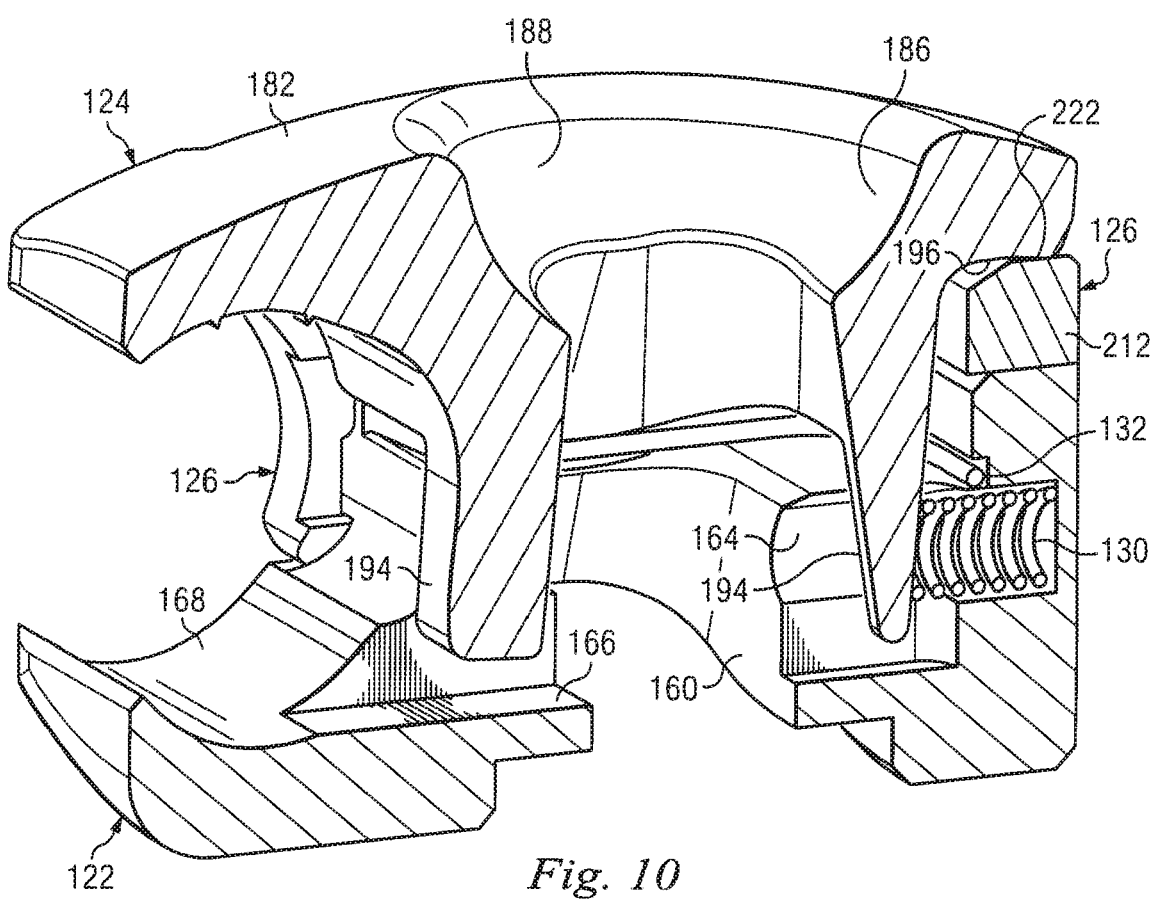
FIG. 10 is an illustration of a cross-section of the clamp of FIG. 8 taken through the lines 10-10 in FIG. 8 according to one exemplary aspect of the present disclosure.

The rear bar 212 connects the two sidewalls 210 and includes a bearing surface 222 that selectively engages the stop surface 196 to prevent rotation of the outer jaw 124 relative to the inner jaw 122. That is, when the rear bar 212 is disposed between the outer jaw 124 and the inner jaw 122, the rear bar 212 may be disposed between the jaws so that the outer jaw 124 cannot pivot. This is best seen in FIG. 10.

Figure 11:
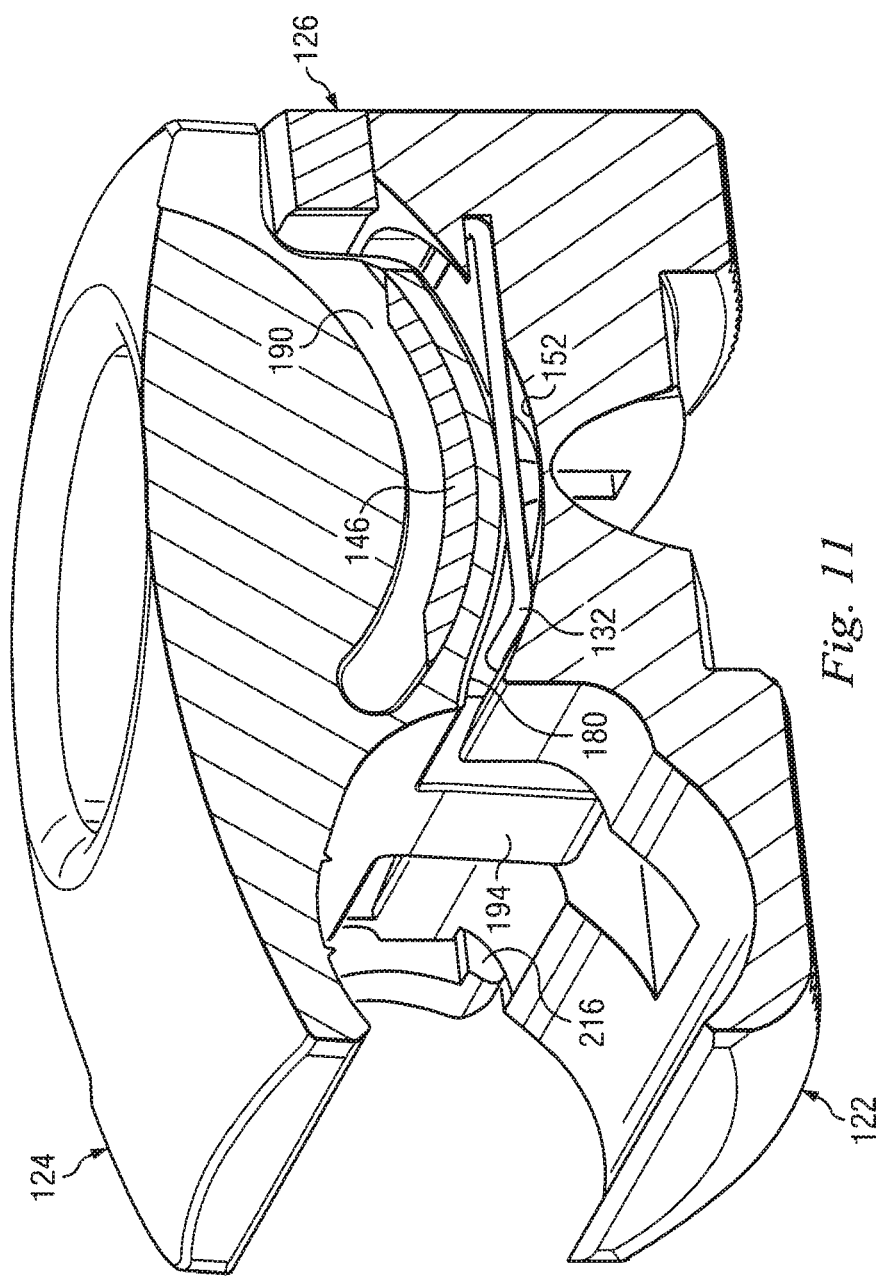
FIG. 11 is an illustration of a cross-section of the clamp of FIG. 8 taken through the lines 11-11 in FIG. 8 according to one exemplary aspect of the present disclosure.
Figure 12:
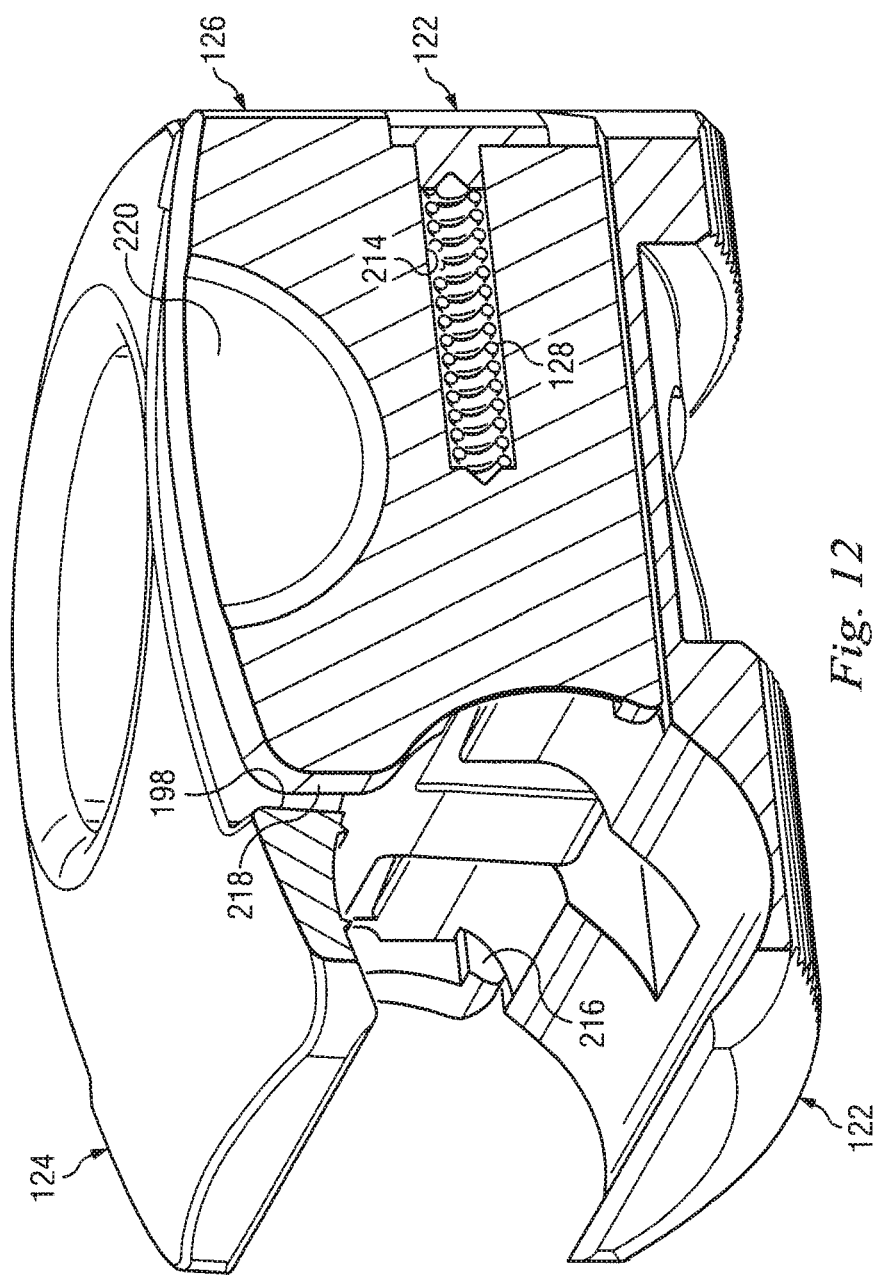
FIG. 12 is an illustration of a cross-section of the clamp of FIG. 8 taken through the lines 12-12 in FIG. 8 according to one exemplary aspect of the present disclosure.
Figure 13:
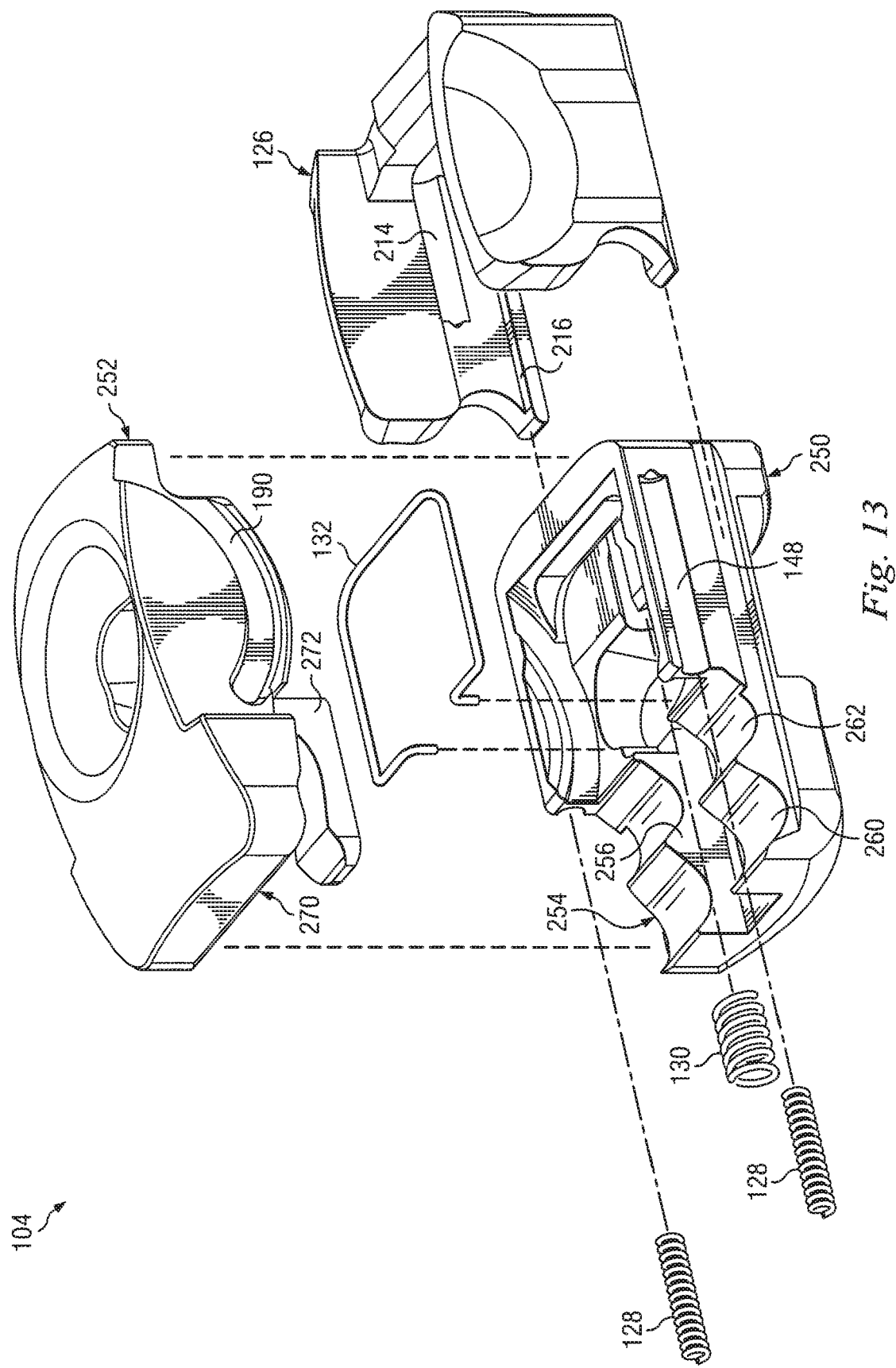
FIG. 13 is an illustration of an exploded isometric view of a clamp of the clamping assembly in accordance with one exemplary aspect of the present disclosure.
Figure 14:
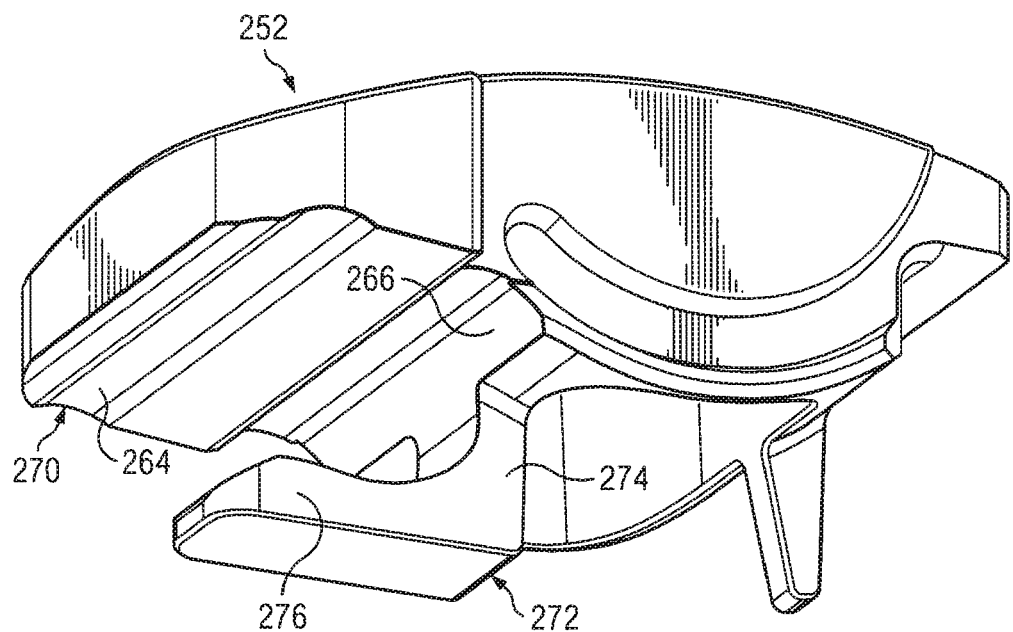
FIG. 14 is an illustration of an outer jaw of the clamp of FIG. 13 according to one aspect of the present disclosure.

The spring wire 132 is disposed between the inner clamp face 180 of the outer jaw 124 and the inner clamp face 138 of the inner jaw 122. It is supported at its corners and spans the depression 152. Here, the spring wire 132 is a substantially square shaped with an opening at one end having angled ends that help secure the wire in place. When the projecting guides 126 are disposed within the track 190, the inner clamp face 180 of the outer jaw 124 sits or rests on the spring wire 132 as shown in FIG. 11. Accordingly, when the clamp is not in a fully locked condition, the spring wire 132 biases the outer jaw 124 away from the inner jaw 122 into the position shown in FIG. 11. However, at the same time, the projecting guides 126 interface with the track 190 and prevent further axial separation of the jaws. This is a provisionally locked condition. As will be described below, when the clamp 104 is placed in a fully locked condition, the wire spring 132 deflects into the depression 152 as the outer jaw 124 is forced further toward the inner jaw 122, and the inner and outer jaws 122, 124 become frictionally engaged. Although shown as a single spring wire in this embodiment, in other embodiments, two or more spring wires are used. These may be placed in a parallel arrangement and extend in the forward-rearward direction or other arrangement. For example, one may be disposed on each side of the hollow or recess 136 described with reference to FIG. 4. In other embodiments, coils springs are used. Other biasing elements are contemplated.

In use, the outer jaw 124 is rotationally engaged with the inner jaw 122 where the projecting guide 146 and the track 190 engage and form a common center of rotation with the spherical pocket 188. The upper facing surface of the track 190 is held against the lower facing surface of the projecting guide 146 by a bias force generated by the slight deflection of the spring wire 132 as shown in FIG. 11. The purpose of this bias force is to provide a preload to hold the jaws 122, 124 in their proper locations while in an open position such that a fixation element may be inserted easily while still allowing for the clearance necessary to affect a clamping load onto the fixation elements once the clamps are tightened. It also ensures that the outer jaw 124 is held in engagement with the spherical washer 108 or head 116 on the post 110, ensuring that the outer jaw 124 rotates about the center of rotation of the washer 108 or the post's spherical head 116. Unlike conventional systems, this separation spring force acts to preload the clamping assembly 100 in the open position as opposed to closed position. This separation force can also be used to preload the entire clamp 102, such that excessive lash is eliminated. Said another way, the spring wire 132 biases the facing surfaces of the inner and outer jaws 122, 124 away from each other. At the same time, as indicated above, the spring wires 132 bias the upper facing surface of the track 190 against the lower facing surface of the projecting guide 146. Other such mechanisms for providing a separation force between the inner and outer jaws 122, 124 are also envisioned such as more conventional spring elements.

The pin clamp 104 is described with reference to FIGS. 13-18. It is similar to the rod clamp 102 described above in many ways and therefore, portions of the description above applies equally to the pin clamp 104 and will not be entirely repeated. The pin clamp 104 includes an inner jaw 250, and outer jaw 252, the latch 126, and the plurality of biasing elements. The biasing elements and the latch are similar to the biasing elements and the latch described with reference to the rod clamp and will not be described further here. For simplicity, similar features of the jaws will be given similar references numbers.

The inner and outer jaws 250, 252 have many similarities to the inner and outer jaws described above, but are configured and arranged to accommodate fixation elements, such as pins, of multiple sizes. This makes the general utility of the clamp greater, as surgeons can use the clamp with more than one size of fixation elements.

As can be seen the inner jaw 250 includes an extended gripping surface portion 254. The gripping surface portion 254 is configured to engage and support a fixation element in the manner discussed above. In this case however, the extended gripping surface portion 254 comprises a first transverse groove 260 and a second transverse groove 262. As will be discussed below, these are designed to accommodate different sized fixation elements. The inner jaw 250 also includes an extended loading pin groove 256. Similar to the loading pin groove 166 discussed above, the extended loading pin groove 256 extends from the central bore to the front end of the inner jaw 250.

The outer jaw 252 includes an extended gripping portion 270 and a loading pin 272. These can be seen in FIGS. 13 and 14. The extended gripping portion 270 is configured to engage and support a fixation element in the manner discussed above and comprises a first transverse groove 264 and a second transverse groove 2660 The loading pin 272 in this embodiment includes a base 274 and a projecting portion 276 angled from the base 274. The loading pin 272 is sized to fit within the loading pin groove 256 when the clamp 104 is in a closed position. The loading pin 272 serves multiple purposes. For example, it acts as a surface on which the fixation element acts to trigger the closure of the clamp. In addition, it cooperates with the extended gripping portion 270 to align the fixation elements with the suitable transverse groove. For example, the loading pin 272 and the extended gripping portion 270 allow a larger fixation element to progress to fit between and be grasped by the first transverse grooves 260, 264, and allows a smaller fixation element to progress to fit between and be grasped by the second transverse grooves 262, 266. In this example, the loading pin 272 does not play a part in the clamping function as it falls into the loading pin groove 256 in the inner jaw 250. The path formed between the loading pin 272 and the transverse grooves 264, 266 is somewhat convoluted to allow for the transverse grooves 264, 266 on the outer jaw 252 to wrap around the fixation elements to provide a more stable capture of the fixation element.

Figure 15:
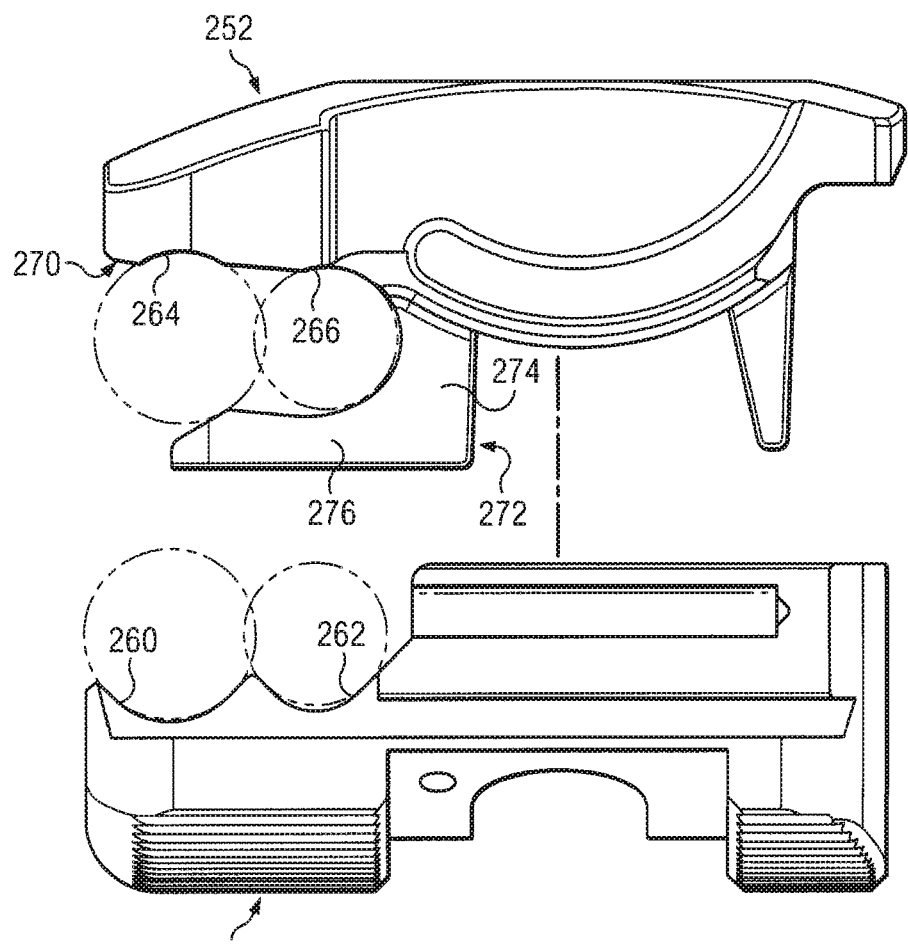
FIG. 15 is an illustration of an outer jaw and an inner jaw of the clamp of FIG. 13 according to one aspect of the present disclosure.

FIG. 15 shows both a 6 mm and a 5 mm construction circle superimposed upon both the inner jaw 250 and the outer jaw 252. These construction circles represent 6 mm and 5 mm fixation elements, respectively. The inner jaw 250 includes the first transverse groove 260 and the second transverse groove 262, with the first transverse groove 260 suited to accept the 6 mm fixation element and the second transverse groove 262 suited to accept the 5 mm fixation element. The grooves 260 and 262 are radially disposed with respect to the outer jaw 252. Similarly, the transverse grooves 264, 266 the outer jaw 252 are disposed as denoted by the corresponding construction circles. These grooves 264, 266 are constructed so that a straight line between the centers of the respective construction circles in each of the inner and outer jaws 250, 252 will be coincident when the jaws 250, 252 are arranged to clamp either of the fixation elements 6 mm or 5 mm. This ensures that the rotation or displacement of the outer jaw 252 with respect to the inner jaw 250 is substantially the same regardless of what size fixation element is chosen, Doing so allows that the other components that make up the pin clamp 104 to each function in the same way leading to a similar, relatively predictable, and relatively reliable design than other designs. It should be noted that grooves for other fixation elements are also contemplated. Further, a pin clamp that includes grooves of only one size is also contemplated. That is, the first transverse groove 260 cooperates with the first transverse groove 264 to securely capture and hold the 6 mm fixation rod in place, Likewise, the second transverse groove 262 cooperates with the second transverse groove 266 to securely capture the 5 mm fixation rod. In this example, although the jaws 250, 252 accommodate a plurality of different sized fixation elements, the relative position of the jaws 250, 252 remain constant. Although described with reference to 5 mm and 6 mm fixation elements, these are only exemplary and other sized fixation rods are contemplated.

Figure 16:
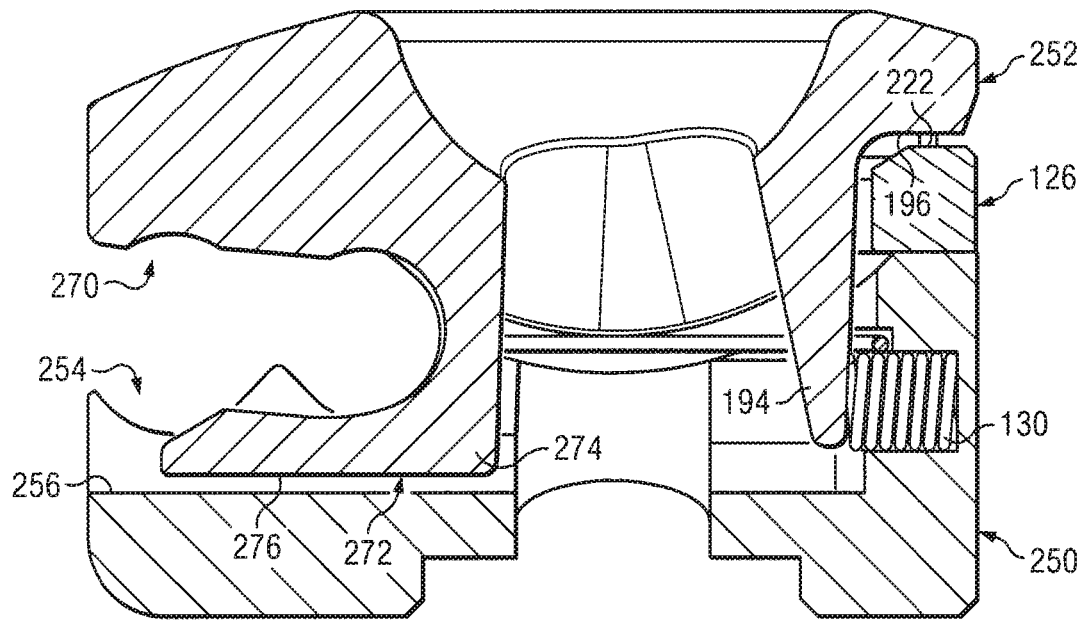
FIG. 16 is an illustration of a cross-sectional view of the clamp of FIG. 13 in a closed position according to one aspect of the present disclosure.
Figure 17:
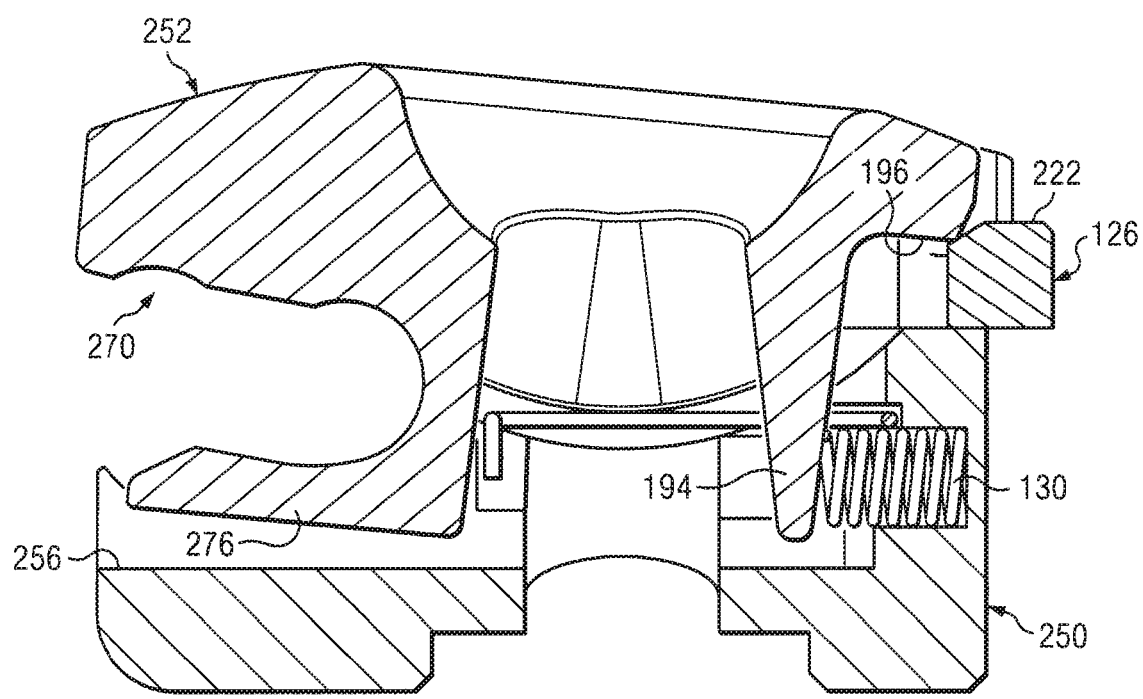
FIG. 17 is an illustration of a cross-sectional view of the clamp of FIG. 13 in an open position according to one aspect of the present disclosure.

FIGS. 16 and 17 show the in clamp 104 in a closed condition and in an open condition respectively. The open condition, which may also be referred to as a cocked state is achieved by pulling back on the latch 126, which is slidably engaged to the inner jaw 250 via the notch 149 and the protruding lip 216. This is done against the force of the biasing members identified as latch springs 128, which are captured in the latch spring seat 148 and partial cylindrical bore 214. When the latch 126 is pulled back a sufficient distance, the bearing surface 222 is moved out from under the stop surface 196 of the outer jaw 252. This allows the outer jaw 252 to be able to rotate relative to the inner jaw 250, The force of the jaw spring 130 bearing on the pin or tab 194 causes the outer jaw 252 to rotate about the inner jaw 250 and the spherical washer 108 or spherical post end 110 into the open state. That is, the gripping surface portions of the inner and outer jaws 250, 252 further separate, opening the jaws to a position wider than the diameter of the fixation element. At this point, if the latch 126 is released, it will come into bearing with the back side of outer jaw 252, effectively holding the jaw and the clamp in the open condition or cocked state.

The closed or latched state occurs as a result of the fixation element insertion process. When the fixation element comes to bear against the hack of the loading pin 272, the result is a torque acting to rotate closed the outer jaw 252. As described above, the outer jaw 252 rotates relative to the inner jaw 250 and relative to the spring wire 132. This rotation displaces the tab 192 relative to the inner jaw 250 against the jaw spring 130, compressing the jaw spring 130. The jaw spring 130 compresses as a result of the rotation. As the outer jaw 252 rotates relative to the inner jaw 250 and latch 126, the rearward portion of outer jaw 252 rises. When the rearward portion of outer jaw 252 is raised up high enough to give clearance to the bearing surface 222 allowing the latch 126 to move forward, the outer jaw 252 becomes locked in the closed position, The bearing surface 222 on the latch 126 prevents the upper jaw 252 from being able to rotate back to an open condition. In some embodiments, the leading end 218 or another leading surface on the latch 126 16 may also come to bear against the fixation element and may serve as a forward stop for the latch 126. Alternatively, the leading end 218 of the latch 126 may abut against the shoulder 198 of the outer jaw 124. The force generated by the latch 126 on the fixation element or on the contact shoulder 198 provides a provisional retention of the fixation element relative in the respective pin or rod jaws 102, 104 and the assembly 100 as a whole. In this provisional retention state, the clamping assembly 100 may easily slide along the inserted fixation elements or rotate about the inserted fixation elements, but the fixation element cannot be removed from the assembly 100 without releasing the latch 126. In addition, the engagement between the fixation elements and the latch may increase the frictional resistance to movement of the clamp relative to the fixation element when the clamp is in the provisional retention state. This prevents or reduces the likelihood of the assembly 100 sliding or rotating on the fixation elements merely by gravitational forces. However, the frictional resistance still permits a surgeon to slide or rotationally adjust the assembly 100 prior to the full lock. In a similar manner, friction from the gripping surface portions and the fixation element increases the frictional resistance to movement in the provisional retention state, This prevents or reduces the likelihood of the assembly 100 sliding or rotating on the fixation elements merely by gravitational forces. However, the frictional resistance still permits the surgeon to slide or rotationally adjust the assembly as desired by the surgeon, prior to the full lock.

The process of releasing the fixation element is identical to the process for opening or cocking previously described. That is, the latch 126 is pulled rearwardly, compressing the latch springs 128 and permitting the jaw spring 130 to rotate the outer jaw 252 relative to the inner jaw 250. The rod clamp 102 operates in a similar fashion as the pin clamp 104 except that it will only accept a fixation element of a single dimension.

As shown in FIG. 3, interposed between rod clamp 102 and the pin clamp 104 about the post 110 is the saddle assembly 106. The saddle assembly 106 is arranged to permit the rod clamp 102 to rotate relative to the pin clamp 104 when the clamping device 100 is in an unlocked or in a provisionally locked condition. In addition, the saddle assembly 106 provides a foundation or base for each of the rod clamps 102 to independently pivot about the pitch axis 130 in FIG. 2 relative to the pin clamp 104.

Figure 18:
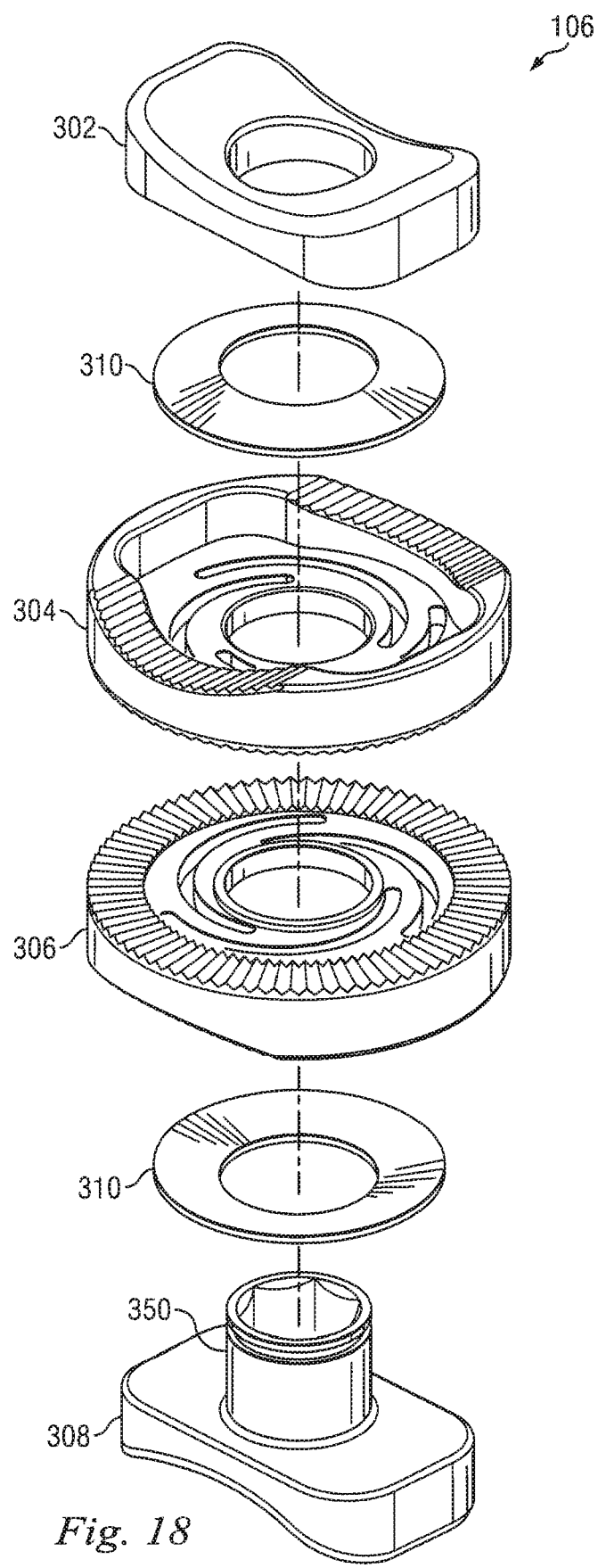
FIG. 18 is an illustration of an exploded view of a saddle assembly according to one aspect of the present disclosure.
Figure 19:
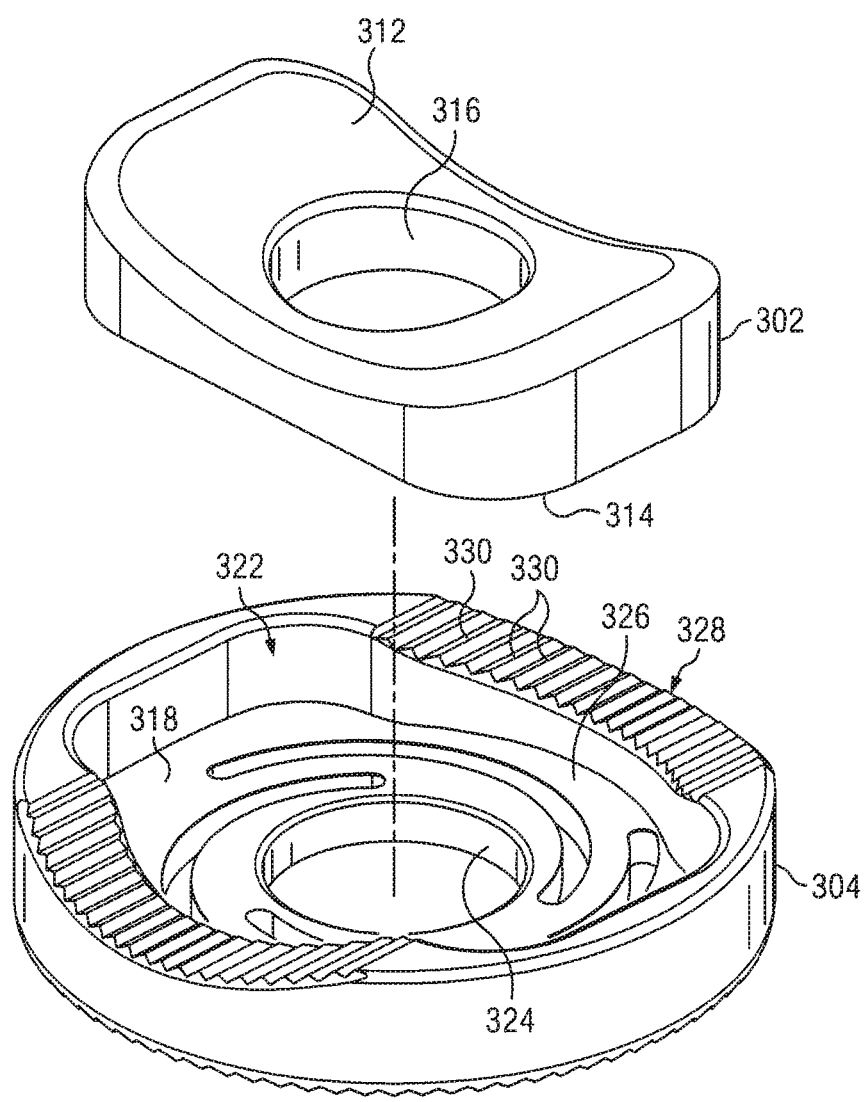
FIG. 19 is an illustration of an exploded configuration of a spacer and saddle base according to one aspect of the present disclosure.
Figure 20:
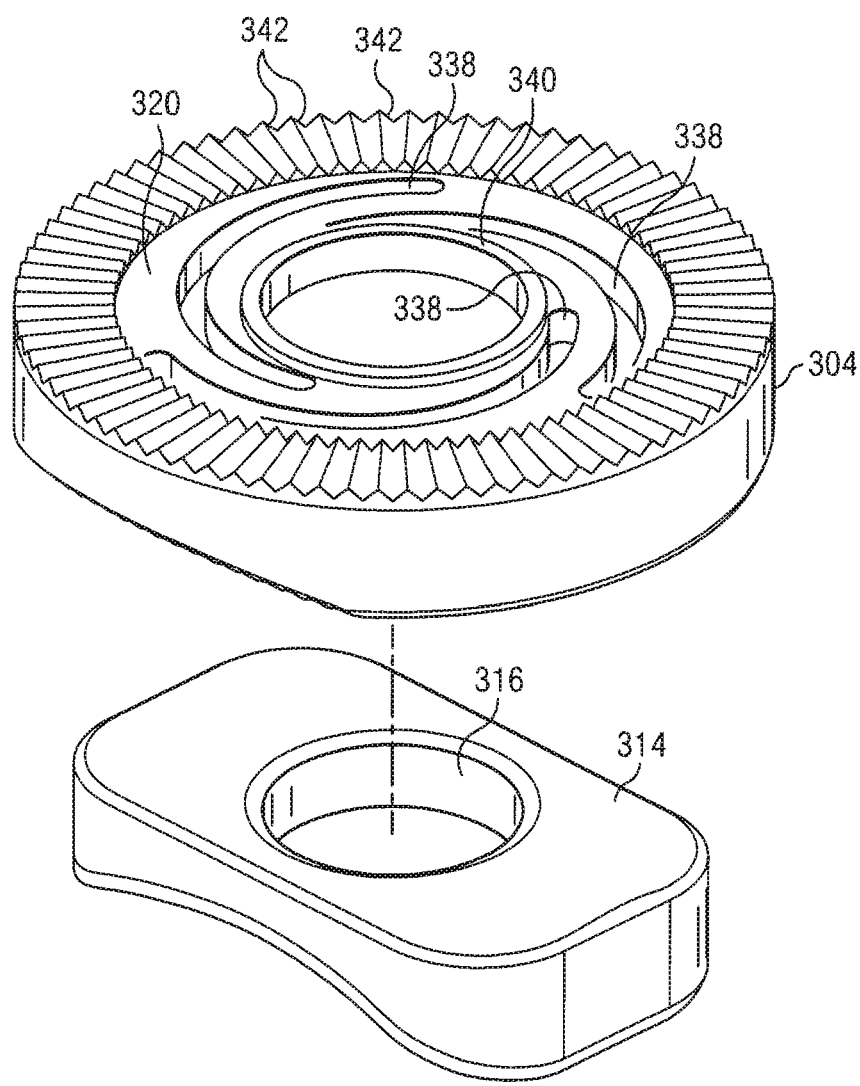
FIG. 20 is an illustration of an exploded configuration of a spacer and saddle base according to one aspect of the present disclosure.
Figure 21:
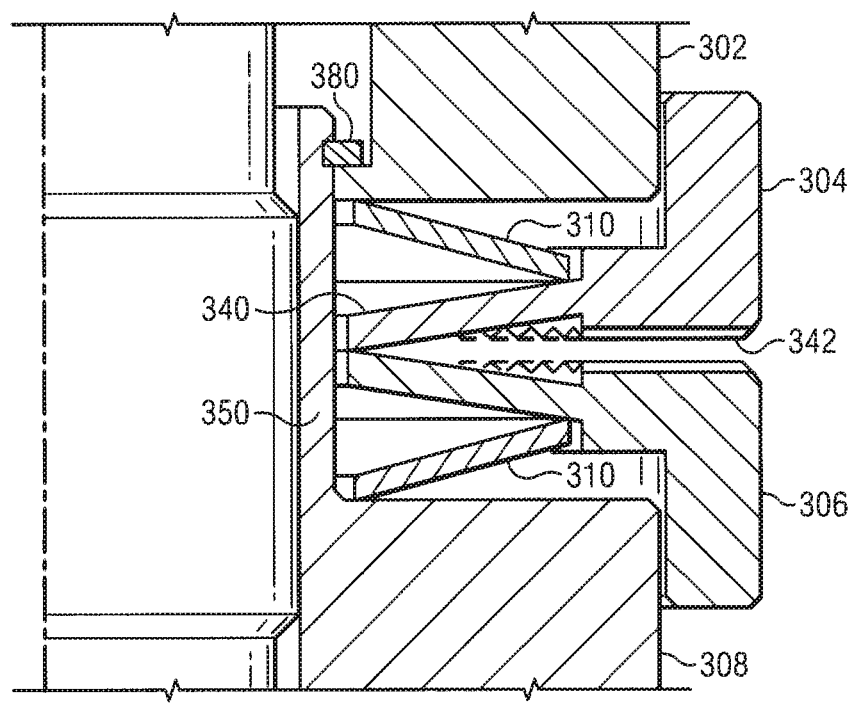
FIG. 21 is an illustration of a cross-sectional view of a portion of the saddle assembly in an assembled configuration according to one aspect of the present disclosure.

FIGS. 18-21 show a first embodiment of the saddle assembly 106. FIG. 18 shows it in an exploded form, FIGS. 19 and 20 shows components of the saddle assembly in greater detail, and FIG. 21 shows a portion of the saddle assembly 106 in cross-section The saddle assembly 106 includes a series of components including a through spacer 302, a first saddle base 304, a second saddle base 306, and a non-circular spacer 308. In the example shown a spring washer 310 is disposed between each of the saddles and the adjacent spacers. These components are described below. The through spacer 302 and the first saddle base 304 are shown in FIGS. 19 and 20. The through spacer 302 is configured to selectively space the saddle base 304 from the inner jaw of the adjacent clamp and prevent relative pivoting between the saddle base 304 and the adjacent clamp when the clamping device 100 is in a fully locked condition. This embodiment will be described as though the through spacer is disposed to engage the rod clamp 102, although the saddle assembly could be rotated so that the through spacer engages the pin clamp 104.

The through spacer 302 is includes a clamp facing side 312 and a saddle facing side 314. The saddle facing side 314 in FIG. 19 can be disposed within a spacer seat 318 of the saddle base 304 (also shown in FIG. 3) and interfaces with the spring washer 310, while the clamp facing side 312 is arranged to face the adjacent inner jaw of the rod clamp 102. The through spacer includes a through hole 316 that extends from the saddle facing side 314 through the jaw facing side 312. The through hole 316 is sized and shaped to permit the through spacer 316 to rotate with its corresponding saddle 304 about the post 110. The through spacer 302 is shaped and configured to sit within the spacer seat 318 to prevent relative rotation between the through spacer 302 and the saddle base 304. In use, the smooth cylindrical surface of the clamp facing side 312 concentrically mates with the cylindrical articulating portion of the outer clamp face 140 of the inner jaw 122 in a manner shown in FIG. 2. The height of the through spacer 302 is selected to cooperate with the depth of the spacer seat 318 to selectively engage and disengage the linear splines of the saddle base 304 with the linear splines on the splined portion of the outer clamp face 104 of the inner jaw 122. Particularly, when the spring washer 310 is in an uncompressed state, the through spacer 302 is offset from the saddle base 304. This offset correspondingly offsets the inner jaw 122 from the saddle base 304 so that the linear splines of the saddle base 304 and the inner jaw 122 are disengaged. In this condition, the inner jaw 122, and thus the entire rod clamp 102, may pivot about the pitch axis 30 relative to the saddle assembly 106, with the cylindrical articulating surface of the outer clamp face 140 of the inner jaw 122 interfacing with the surface 312 on the through spacer 302. When the clamping assembly 100 is placed in the fully locked condition, the spring washer 310 compresses, the offset is reduced or eliminated, and the through spacer 302 seats more completely or fully within the spacer seat 318. Likewise, the inner jaw 122 moves closer to the saddle base 304 until the linear splines on the cylindrical surface of the inner jaw 122 engage the linear splines on a clamp interfacing portion 328 of the saddle base 304. This locks the clamp 102 to the saddle assembly 106, preventing further pivoting rotation about the axis.

Still referring to FIGS. 19-21, the saddle base 304 includes an inner facing side 320 and an outer facing side 322. The inner facing side 320 is shown in FIG. 20 and the outer facing side 322 is shown in FIG. 19. Starting with the outer facing side 322, the saddle base 304 includes a centrally disposed through hole 324, a bias member or spring washer seat 326, and a clamp interfacing portion 328 with interdigitations 330. The through hole 324 is a central bore extending from the inner facing side 320 to the outer facing side 322. It is sized and configured to receive the post 110 and is sized to permit the saddle base 304 to freely rotate about the post 110. The spring washer seat 326 and the clamp interfacing portion 328 are concentrically disposed about the through hole 324. The spring washer seat 326 is sized to receive the spring washer 310. The clamp interfacing portion 328 is disposed between the spring washer seat 326 and the saddle base perimeter and is configured to selectively engage with and provide positive retention from relative pivot movement about the pitch axis 30 when the saddle assembly 106 and the rod clamp 102 are locked together, thereby preventing relative rotation between the saddle assembly 106 and the clamp 102 when the clamping device 100 is in a fully locked condition. In this example, the clamp interfacing portion 328 includes friction enhancing features such as interdigitations or splines that engage corresponding friction enhancing features such as interdigitations or splines on the clamp 102 when the clamping device 100 is fully locked. It is worth noting that the spring washer 310 is disposed between the saddle base 304 and the through spacer 302.

The inner facing surface 320 of the saddle base 304 faces a corresponding inner facing surface of the saddle base 306. Each of these have friction enhancing features, such as radial splines 342, configured to engage and prevent relative rotation between the saddle bases. Other friction enhancing features are contemplated. In the example shown, the saddle base 304 is formed with a built-in, flexible, biasing function that biases the saddle base 304 away from the saddle base 306. This biasing function is formed by a plurality of grooves 338 formed in the base that permit the center portion 340 of the saddle base 304 to elastically displace relative to the saddle perimeter when a load is applied. FIG. 21 shows a portion of this in cross-section. In the example shown, when in a neutral condition, the center portion 340 of the saddle base 304 projects at least to or beyond a plane formed through the friction enhancing features 342, shown as splines. Accordingly, in a neutral condition, the center portion 340 engages the opposing center portion of the saddle base 306 and offsets the friction enhancing features 342 from the opposing saddle base 306 as shown in FIG. 21. Under sufficient load, the center portion 340 may deflect to a position below the plane through the friction enhancing features 342. This enables the friction enhancing features 342 to engage and cooperate with the friction enhancing features of the opposing saddle base 306. The saddle base 306 is formed in the same manner as the saddle base 304 and will not be described further here.

The non-circular spacer 308 cooperates with the saddle base 310 and performs the same interfacing function as the through spacer 302. In addition, the non-circular spacer 308 includes a protruding boss 350 with an inner non-circular shape, shown in this example as a hex shape, that matches the noncircular shape of the post 110 shown in FIG. 3. Accordingly, when the non-circular spacer 308 is disposed on the post 110, it may be restricted from rotating about the post 110. The saddle bases 304, 306 and the through spacer 302 all fit about the boss 350 and may be configured to rotate relative to the boss 350. Accordingly, the through spacer 302 and the saddle base 304 may be configured to rotate relative to the non-circular spacer 308 and the post 110. The saddle base 306 may be restricted from rotation about the boss 350 because it receives a portion of the non-circular spacer 308 into a seat that prevents relative rotation. Accordingly, in the example shown, the through spacer 302 and the saddle base 304 may rotate with the rod clamp 102 about the post 110. Likewise, the non-circular spacer 308 and the saddle base 306 may rotate with the pin clamp 104 about the post 110. In other respects, the non-circular spacer 308 may include features similar to those described above with reference to the through spacer and may be configured to engage the pin clamp 104.

The saddle assembly 106 may be configured to also include a retaining ring 380 that may permit the saddle assembly 106 to be independently assembled as a complete subassembly. This retaining ring 380 is shown in FIG. 21. The retaining ring may permit the saddle assembly to be preloaded by preloading the washer springs and the flexible biasing portions of the saddle bases as described further below.

Figure 23:
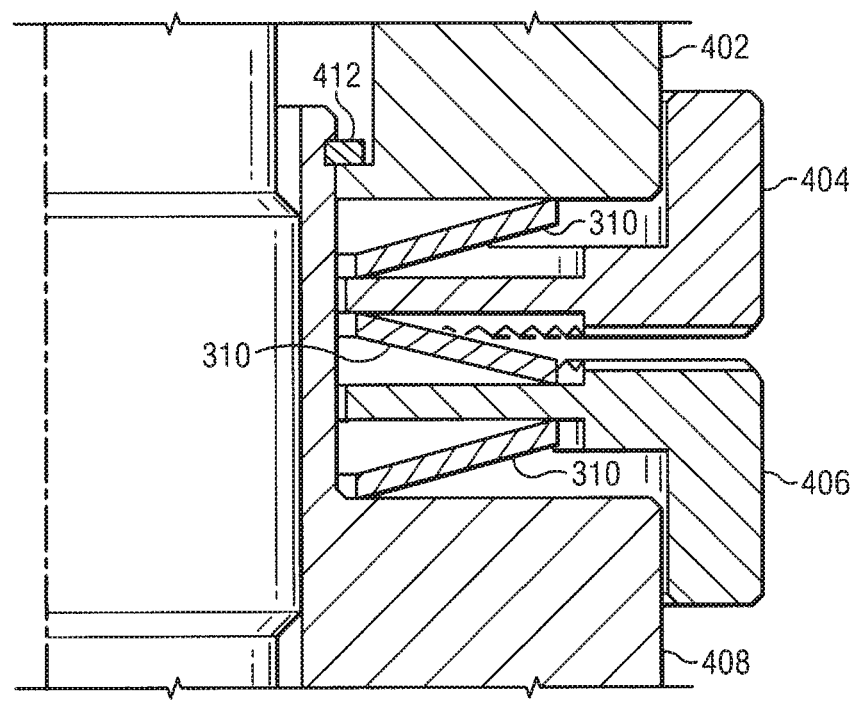
FIG. 23 is an illustration of a cross-sectional view of a portion of the saddle assembly in an assembled configuration according to one aspect of the present disclosure.
Figure 22:
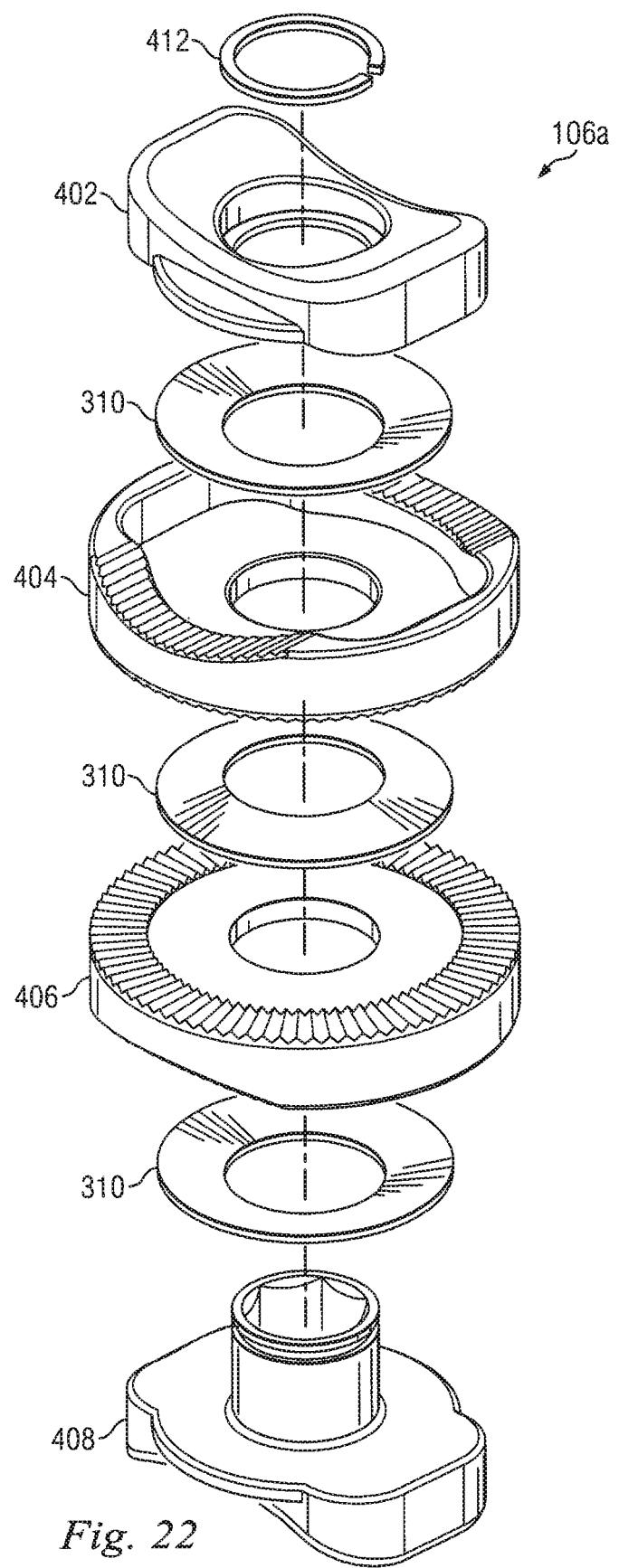
FIG. 22 is an illustration of an exploded view of a saddle assembly according to one aspect of the present disclosure.

In an alternative embodiment shown in FIGS. 22 and 23, and referenced herein as 106a, the saddles include solid bases, and they are selectively separated by an additional spring washer 310. This saddle assembly includes a through spacer 402, two saddle bases 404, 406, and a non-circular spacer 408, with spring washers 310. They are similar in many ways to the components described above, and their descriptions will not be repeated here. In addition, the saddle assembly 106a also includes a retaining ring 412 that engages a boss on the non-circular spacer 408 and maintains the saddle assembly 106a in a single assembly. This can be easily seen in FIG. 23. This may enable easier assembly of the overall clamping assembly 100.

In one example, the spring washers 310 in the saddle assembly 106 and 106a are selected to be high spring rate washers, As used herein, the term "high spring rate" is intended to include spring rate values that exceed the operational forces applied to latch or provisionally secure fixation elements into the inner and outer jaws and that are sufficient to maintain interdigitating surfaces in a spaced apart relationship. In one example, this is a spring rate of about 30 lbs/inch or greater. In some examples, the spring washers 310 have a spring rate of about 50 lbs/inch or greater. In this example, the spring washers are high spring rate washers resulting in a high force, but low travel.

Because of the high spring rate, all latching is accomplished without any degree of three being applied on the jaws of the clamps 102, 104 by the spring washers 310 in a manner that contributes to the latching. As such, for purposes of the latching onto a fixation element, the saddle assembly 106, 106a has a stiffness such that it may be treated as a rigid body because it does not play a role in the latching.

Some prior systems include a clamping assembly having a spring element that acts to force inner and outer jaws together to create a clamping interaction. In this disclosure, the spring washers 310 act in a direction that would, only if an excessive load was applied to the saddle assembly 106, act to force the inner and outer jaws together. However, in the embodiment shown, the saddle assembly 106, 106a is preloaded to an amount greater than that which would cause complete deflection of spring wires 132. Accordingly, if loads that caused deflection of the spring washers 310 or the saddle bases 304, 306 were present, then the wire springs 132 in the pin and rod subassemblies 101 and 103 would necessarily already be completely deflected (because of their significantly lower spring rates), rendering the rod and pin clamps 102, 104 inoperable because they would not be able to accept a fixation element. Instead of assisting in the insertion process or the clamping process, the spring washers 310 and the biasing portions of the saddle bases 304, 306 enable smooth reduction of the fracture after the fixation elements are inserted and latched. In fact, there is no mechanism available to provide such a preload other than the clamping elements that as stated would render the clamp inoperable if they were to be tightened prior to insertion of a fixation element.

In one example, the initial preload is set so that the non-circular spacer 308, 408 isolates the saddle assembly 106, 106a from the clamps 102, 104. In one example of the system 100, the saddle assembly 106, 106a is preloaded. Accordingly displacement occurs only when loading on the system 100 exceeds the preload. This preload may be established so that only loads exceeding, for example, 260 k lbF/in create additional displacement. In one embodiment, the 260 k lbF/in is the spring rate of the non-circular spacer. By using such a preload, the spring washers 310 and the biasing portions of the saddle bases 304, 306 therefore will contribute forces for clamping jaws together only after 260 k lbF/in is reached. Other thresholds are contemplated. Since the clamps 102, 104 will already be closed by that time, the saddle assembly spring washers 310 and the biasing portions of the saddle bases 304, 306 play no role in the jaw clamping process, but act as rigid elements during the jaw clamping process.

Below is a table comparing the difference in the forces and stored energy applied by the latch springs 128 and the jaw spring 130 when the clamps 102, 104 are in an open position and when in a closed position. It is worth noting that conventional devices have an open condition, where springs have a first lower stored energy (spring displacement is low or zero) and a closed condition where springs have a second higher stored energy (spring displacement is relatively higher). That is, the process of inserting a bar into the clamp compresses the spring, resulting in an increase in spring force. However, the device of the present disclosure shows the energy introduced into the system and that the latch springs 128 are compressed when the latch 126 is pulled rearwardly and the clamp is in an open condition.

table shows the stored energy value for the latch springs 128 in a closed condition. The closed condition has a lower stored energy value. Thus, the device 100 has less stored energy in a closed condition than the open condition. It should also be noted that the energy is acting in the direction of insertion instead of in the direction of the post. In this example, the direction of insertion is transverse to the direction of the post.

The jaw spring 130 does not act on the bar or pin, and it could be ignored. However, for completeness, it is included. Even taking the jaw spring into account, the Total Energy Comparison for the springs of the rod clamp are 0.183 in-lbF in the closed condition and 0.259 in-lbF in the open condition.

It should be noted that the spring parameters may vary from those used in the above example. For example, the lengths and rates may differ among different clamps. Even still, the arrangement may provide the advantage of a lower spring energy in the clamped position than when in the open position.

In use, the clamping assembly 100 may be in the open position to start or may be set in the open position be pulling the latch 126 relative to the inner and outer jaws of one of the pin or rod clamps 102, 104. For explanatory purposes, the operation will be described relative to the rod clamp 102. Pulling the latch 126 compresses the latch springs 128, increasing the potential energy in the clamp. With the latch 126 pulled back, the outer jaw 124 has clearance to rotate relative to the latch 126 and the inner jaw 122. With the latch 126 pulled back, the jaw spring 130 biases the outer jaw 124 relative to the inner jaw 122 to the open position. Particularly, once the latch 126 is pulled back, the jaw spring 130 acts against the tab 192 to rotatably displace the whole outer jaw 124 relative to the inner jaw 122. The latch 126 is held in its displaced position by interference with the rear portion of the outer jaw 124. Because the latch 126 is pulled back, the latch springs 128 are compressed, having high potential or stored energy.

With the clamp 102 in the open position, the fixation element 12 may be introduced as described above. That is, the fixation element is introduced between the inner and outer jaws 122, 124. These are arranged to have an opening with a width greater than the width of the fixation element. Accordingly, the fixation element can pass through the opening without changing the spring energy levels. When the fixation element is between the jaws 122, 124, further

| Spring | Open | Closed |
| --- | --- | --- |
| Latch Spring (each) | Installed Length = 0.250 in | Installed Length = 0.330 in |
| Rate = 4.11 lbF/in | Load = 1.03 lbF | Load = 0.70 lbF |
| Free Length = 0.500 in | Energy = 0.129 in-lbF | Energy = 0.060 in-lbF |
| Jaw Spring | Installed Length = 0.240 in | Installed Length = 0.130 in |
| Rate = 8.78 lbF/in | Load = 0.09 lbF | Load = 1.05 lbF |
| Free Leagth = 0.250 in | Energy = 0.0005 in-lbF | Energy = 0.063 in-lbF |

Based on the values, the total Energy Comparison for two latch springs and one jaw spring is:

Open=2×0.129+0.0005=0.259 in-lbF

Closed=2×0.060+0.063=0.183 in-lbF

Accordingly, the total energy is lower when the latch is closed. The table above shows the stored energy value for the latch springs when the clamp is in an open condition. When the latch 126 is released and moved forward to a closed position, some but not all the energy is released. The insertion causes the fixation element to engage the loading pin 272 and displace the outer jaw 124. The outer jaw 124 then begins to rotate about the spherical washer 108 or the spherical head 116 of the post 110. Rotation of the outer jaw 124 triggers the spring-loaded latch 126, moving the jaws 122, 124 from the open to the closed position, and capturing the fixation element between the inner and outer jaws 122, 124. As this occurs, the energy stored within the compressed latch springs 128 is released. Accordingly, the amount of energy stored within the subassembly decreases when fixation elements are inserted, as a result of the triggering mechanism. However, as indicated in the table above, a portion of the energy still remains. This remaining portion of energy provides a provisional clamping force on the fixation element.

When the clamp 102 is in the closed position, with a fixation element secured therein, the clamp 102 is in the provisional retention state. In this state, the fixation elements cannot be removed from the clamp 102, but the clamp 102 is still loose enough for adjustable connection.

In one example, the clamp 102 still frictionally engages the fixation element with enough force to prevent loose sliding resulting solely from gravity, Accordingly, a surgeon can manipulate the fixation frame or slide or rotate the clamping assembly 100 on the fixation elements to a desired position. Because the spring wire 132 biases the jaws 122, 124 to grip the fixation element, the assembly 100 is not floppy or does not move merely as a result of gravitational forces, but requires a surgeon to manipulate it.

When the surgeon has placed the fixation frame or the clamping assembly 100 in a desired position, he may fully lock it down to prevent further adjustment and further movement. This is done by tightening the nut 112. As the nut 112 tightens on the post 110, the rod and pin clamp 104, 102 begin to compress. Because the spring wires 132 in the rod and pin subassemblies have lower spring rates than the spring washers 310 in the saddle assembly 106, these deflect first as the nut 112 is tightened. As the nut 112 tightens, the inner and outer jaws 122, 124 move toward each other compressing the spring wires 132, and increasing the frictional gripping force of the jaws 122, 124 on the fixation elements until the outer jaw and the inner jaw are substantially rigid. This occurs as the outer jaw 124 is compressed against the fixation element and the latch 126. Continued tightening of the nut 112 results in higher forces that act to compress the high spring rate spring washers 310 in the saddle assembly 106. As these compress, the interdigitations of the saddle bases 304, 306 and the inner jaw 122, 250 engage or mechanically interfere to eliminate or reduce pivoting rotation of the clamps relative to the saddle assembly 106. At the same time, the facing interdigitations of the two saddle bases 304, 306 engage or mechanically interfere to eliminate or reduce relative rotation of the saddles bases 304, 306 about the post 110, thereby fixing the rotational position of the pin and rod subassemblies 102, 104 relative to each other. In this condition, the clamping assembly 100 is in a fully locked position. Disassembly of the fixation frame assembly can be achieved by loosening the nut 112 to return the assembly 100 to the provisional retention position and pulling back the latch 126 to pivot the upper jaw 124 and release the fixation element.

In this embodiment, the entire mechanism of retention operates entirely independently of the mechanism for locking. That is, all the energy contained in the provisional clamping is independent of and separate from the spring energy used to fully lock down or fully clamp the fixation element. in addition, as is apparent from the drawings, the spring forces that drive the triggering mechanism and capture the fixation element act in a direction transverse to the post direction, instead of along the post direction. In contrast, the spring forces that drive the locking mechanism are all acting in a direction parallel to the post direction. Thus, each of the pin clamp 104, the saddle assembly 106, and the rod clamp 102 act independently of one another and can operate as desired without the aid of the others.

While it is contemplated that some embodiments of the assembly 100 are single use devices for medical applications, one of the advantages of the assembly 100 is its ability to release and receive an alternative rod or pin. For example, pulling the latch not only releases a fixation bar held in the pin or rod subassemblies, but also places the assembly in the open condition to receive another pin or fixation rod. This becomes particularly useful as surgeons or other health care professionals set up the external fixation system with multiple rods and multiple pins. If the health care profession decides to modify the arrangement of the fixation system, he or she can easily do so by pulling the clamp to release the bar or pin, and then conveniently clamp onto an alternate bar or pin without further clamp manipulation. The assembly 100 can then be locked using the locking subassembly as discussed above. Although shown as springs of different types, including coil springs, washer springs, and wire springs, the biasing members may be other types of biasing members.

In one aspect, the present disclosure is directed to an external fixation clamp that has the ability to retain without release at least one fixation element, where the act of insertion is carried out on a clamp in a state where the aperture through which the fixation element must pass is greater in width at all points than the fixation element through its greatest cross section.

In another aspect, the present disclosure is directed to an external fixation clamp that has the ability to retain without release at least one fixation element, where the act of insertion of the fixation element results in a trigger event whereby energy stored within the clamp is released, a portion of which remains to provide a provisional clamping force on the fixation element.

In another aspect, the present disclosure is directed to an external fixation clamp that has the ability to retain without release at least one fixation element where the mechanism of retention is separate from the mechanism of clamping.

In another aspect, the present disclosure is directed to an external fixation clamp that has the ability to retain without release at least one fixation element where the removal of the clamping element from the fixation element results in the clamping element being ready without further adjustment to accept another fixation element.

In another aspect, the present disclosure is directed to an external fixation clamp that has the ability to retain without release at least one fixation element that has the ability to generate a variable amount of resistance to motion that is a function of the degree to which the clamp is tightened, and where that amount of adjustment is invariant with respect to all external action applied to the clamp except a change in the amount of tightening of the clamping element.

In another aspect, the present disclosure is directed to an external fixation clamp that has the ability to retain without release at least one fixation element where having the amount of stored energy within the clamp becomes less as fixation elements are inserted.

In another aspect, the present disclosure is directed to an external fixation clamp that has the ability to retain without release at least one fixation element where a plurality of cylindrical sizes can be accommodated individually where the relative positions of the jaw elements remains a constant.

In another aspect, the present disclosure is directed to an external fixation clamp that has the ability to retain without release at least one fixation element and whose natural state (the one having the least stored energy) is the closed state.

In another aspect, the present disclosure is directed to an external fixation clamp that has the ability to retain without release at least one fixation element whose clamping element has a tightening interface that is in a plurality of sections spherical in nature.

In another aspect, the present disclosure is directed to an external fixation clamp for receiving a fixation element. The fixation clamp comprises a jaw subassembly that includes an inner jaw and an outer jaw cooperatively arranged with the inner jaw to capture a fixation element. The inner and outer jaws may be movable between an open position that permits the fixation element to be placed between the inner and outer jaws and a closed position that restricts removal of the fixation element from between the inner and outer jaws, The jaw subassembly also includes a latch assembly cooperating with the inner and outer jaws to secure the jaws in a closed position. The latch assembly comprises a latch and a latch spring, where the latch spring has a first higher level of stored energy when the inner and outer jaws are in the open position and a second lower level of stored energy when the inner and outer jaws are in the closed position.

In one aspect, the latch is configured to linearly translate relative to one of the upper and lower jaw pairs and the change in stored energy is a result of compressing a coil spring during the linear translation of the latch.

In another aspect, the present disclosure is directed to an external fixation clamp for receiving a fixation element. It includes an inner jaw having a first seat for a first fixation element having a first size and having a second seat for a second fixation element having a second size different than the first size. It also includes an outer jaw having a third seat for the first fixation element of the first size and a fourth seat for the second fixation element of the second size.

In another aspect, the present disclosure is directed to an external fixation clamp for receiving a fixation element. It includes an inner jaw and an outer jaw cooperatively arranged with the inner jaw to capture a fixation element. The inner and outer jaws may be movable between an open position that permits the fixation element to be placed between the inner and outer jaws and a closed position that restricts removal of the fixation element from between the inner and outer jaws. The clamp also includes a biasing element disposed between the first and second jaws and configured to bias the first and second jaws to the open position.

The other aspects of these figures is to demonstrate that the force that acts on the springs is born by the cocking process and not the insertion process and that ultimately there is less stored energy in the clamping assembly after insertion that there was prior to insertion. This too is a departure from the prior art and as already mentioned this decouples the requirement of the clamping elements from the latching elements leading to a consistent easier to operate clamping assembly.

What is claimed is:

1. A clamping device for clamping fixation elements of an external fixation system, the clamping device comprising:
   a post having a yaw axis and a spherical head at a first end opposite a second end;
   first and second clamps secured to the post and configured to rotate about the yaw axis; and
   a tightening component operatively coupled to the second end of the post, wherein the first clamp comprises:
   first and second jaws cooperatively arranged to capture a fixation element therebetween, the fixation element having a roll axis along which the first clamp is configured to translate and about which the first clamp is configured to rotate; and
   a sliding latch configured to be linearly translated relative to one of the first and second jaws to set the first and second jaws in an open position and in a provisionally locked position; and
   a jaw spring that is relatively compressed when the first and second jaws are in the provisionally locked position and that is relatively uncompressed to bias a clamping portion of one of the first and second jaws away from a clamping portion of the other of the first and second jaws when the first and second jaws are in the open position, and
   wherein the tightening component is configured in a manner that an action of tightening the tightening component simultaneously fully locks a position and orientation of the clamping device relative to the post and the fixation element.

2. The clamping device of claim 1, further comprising a latch biasing member arranged and configured to bias the sliding latch to set the first and second jaws in the provisionally locked position.

3. The clamping device of claim 2, wherein the latch biasing member has a first higher level of stored energy when the first and second jaws are in the open position and a second lower level of stored energy when the first and second jaws are in the provisionally locked position.

4. The clamping device of claim 2, wherein each of the first and second jaws comprises a clamping portion and a rear portion opposite the clamping portion, and, wherein the latch biasing member comprises at least one spring, the at least one spring being relatively uncompressed to bias the sliding latch to be disposed toward the clamping portions of the first and second jaws when the first and second jaws are in the provisionally locked position and being relatively compressed when the sliding latch is disposed toward the rear portions of the first and second jaws when the first and second jaws are in the open position.

5. The clamping device of claim 1, wherein the tightening component comprises a threaded nut threadably engaging threads at the second end of the post.

6. The clamping device of claim 1, wherein a first clamping portion of one of the first and second jaws comprises a first seat for a first fixation element having a first size and a second seat for a second fixation element having a second size different than the first size.

7. The clamping device of claim 6, wherein a second clamping portion of the other of the first and second jaws comprises a third seat for the first fixation element of the first size and a fourth seat for the second fixation element of the second size.

8. The clamping device of claim 1, wherein the sliding latch comprises first and second wall portions connected by an extending bar portion.

9. The clamping device of claim 1, wherein the jaw spring extends along a jaw spring axis that is at an angle relative to the yaw axis.

10. A clamping device for clamping fixation elements of an external fixation system, the clamping device comprising:
   a post having a yaw axis and a spherical head at a first end opposite a second end;
   first and second clamps secured to the post and configured to rotate about the yaw axis;
   a saddle assembly disposed between the first and second clamps; and
   a tightening component operatively coupled to the second end of the post, wherein at least one of the first and second clamps comprises:
   first and second jaws cooperatively arranged to capture a fixation element therebetween, the fixation element having a roll axis along which the first clamp is configured to translate and about which the first clamp is configured to rotate; and a sliding latch configured to be linearly translated relative to one of the first and second jaws to set the first and second jaws in an open position and in a provisionally locked position; and a jaw spring that is relatively compressed when the first and second jaws are in the provisionally locked position and that is relatively uncompressed to bias a clamping portion of one of the first and second jaws away from a clamping portion of the other of the first and second jaws when the first and second jaws are in the open position, and wherein the tightening component is configured in a manner that an action of tightening the tightening component simultaneously fully locks a position and orientation of the first and second clamps relative to the post and the fixation element.

11. The clamping device of claim 10, further comprising a latch biasing member arranged and configured to bias the sliding latch to set the first and second jaws in the provisionally locked position.

12. The clamping device of claim 11, wherein the latch biasing member has a first higher level of stored energy when the first and second jaws are in the open position and a second lower level of stored energy when the first and second jaws are in the provisionally locked position.

13. The clamping device of claim 11, wherein each of the first and second jaws comprises a clamping portion and a rear portion opposite the clamping portion, and, wherein the latch biasing member comprises at least one spring, the at least one spring being relatively uncompressed to bias the sliding latch to be disposed toward the clamping portions of the first and second jaws when the first and second jaws are in the provisionally locked position and being relatively compressed when the sliding latch is disposed toward the rear portions of the first and second jaws when the first and second jaws are in the open position.

14. The clamping device of claim 10, wherein the tightening component comprises a threaded nut threadably engaging threads at the second end of the post.

15. The clamping device of claim 10, wherein a first clamping portion of one of the first and second jaws comprises a first seat for a first fixation element having a first size and a second seat for a second fixation element having a second size different than the first size.

16. The clamping device of claim 15, wherein a second clamping portion of the other of the first and second jaws comprises a third seat for the first fixation element of the first size and a fourth seat for the second fixation element of the second size.

17. The clamping device of claim 10, wherein the sliding latch comprises first and second wall portions connected by an extending bar portion.

18. The clamping device of claim 10, wherein the jaw spring extends along a jaw spring axis that is at an angle relative to the yaw axis.

* * * * *